US012745966B2

(12) United States Patent
Sawanoi et al.

(10) Patent No.: US 12,745,966 B2
(45) Date of Patent: Sep. 29, 2026

(54) ELECTRONIC SPHYGMOMANOMETER AND METHOD FOR DETERMINING ATRIAL FIBRILLATION IN AN ELECTRONIC SPHYGMOMANOMETER

(71) Applicant: OMRON HEALTHCARE CO., LTD., Muko (JP)

(72) Inventors: Yukiya Sawanoi, Kyoto (JP); Terumasa Naito, Kyoto (JP); Hiroyuki Kanda, Kyoto (JP); Yuta Kudo, Kyoto (JP); Tatsunori Ito, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 614 days.

(21) Appl. No.: 18/328,814

(22) Filed: Jun. 5, 2023

(65) Prior Publication Data

US 2023/0309934 A1 Oct. 5, 2023

Related U.S. Application Data

(63) Continuation of application No. PCT/JP2021/045149, filed on Dec. 8, 2021.

(30) Foreign Application Priority Data

Dec. 22, 2020 (JP) ................................ 2020-212869

(51) Int. Cl.

*A61B 5/00* (2006.01)
*A61B 5/022* (2006.01)
*A61B 5/0225* (2006.01)

(52) U.S. Cl.

CPC ........ *A61B 5/7289* (2013.01); *A61B 5/02225* (2013.01); *A61B 5/0225* (2013.01)

(58) Field of Classification Search

CPC . A61B 5/7289; A61B 5/02225; A61B 5/0225; A61B 5/361; A61B 10/00

(Continued)

(56) References Cited

U.S. PATENT DOCUMENTS 5,865,756 A * 2/1999 Peel, III ............. A61B 5/02225 600/490
5,895,359 A * 4/1999 Peel, III ............. A61B 5/02225 600/494

(Continued)

FOREIGN PATENT DOCUMENTS

CN 1457743 A * 11/2003 ......... A61B 5/02225
CN 101073496 A * 11/2007

(Continued)

OTHER PUBLICATIONS

Translation of CN 101073496 (Year: 2007).*

(Continued)

*Primary Examiner* — Navin Natnithithadha
(74) *Attorney, Agent, or Firm* — Oliff PLC

(57) ABSTRACT

An electronic sphygmomanometer includes a cuff pressure control unit, a pressure detection unit, and a blood pressure measurement unit that extracts a pulse wave signal and measures blood pressure based on the pulse wave signal. A pulse wave interval calculation unit obtains a data group representing pulse wave intervals based on the pulse wave signal obtained only in one depressurization process for a subject for each one measurement occasion. A determination unit aggregates data groups for three or more measurement occasions to obtain an average value of the pulse wave intervals, and determines whether or not there is a possibility that atrial fibrillation occurred based on whether or not there is data of an irregular pulse wave exceeding an allowable range with respect to the average value.

6 Claims, 14 Drawing Sheets

(58) Field of Classification Search
USPC .................................................. 600/490–504
See application file for complete search history.

(56) References Cited

U.S. PATENT DOCUMENTS

| | | | | | |
|---|---|---|---|---|---|
| 5,931,790 | A * | 8/1999 | Peel, III | A61B 5/02225 600/494 | |
| 6,527,725 | B1 * | 3/2003 | Inukai | A61B 5/0225 600/494 | |
| 8,348,851 | B2 * | 1/2013 | Inoue | A61B 5/02141 600/493 | |
| 2004/0186386 | A1 * | 9/2004 | Kolluri | A61B 5/022 600/500 | |
| 2005/0004477 | A1 * | 1/2005 | Friedman | A61B 5/349 600/485 | |
| 2010/0210957 | A1 * | 8/2010 | Inoue | A61B 5/02141 600/493 | |
| 2017/0135585 | A1 | 5/2017 | Liu et al. | | |

FOREIGN PATENT DOCUMENTS

| | | | | | |
|---|---|---|---|---|---|
| CN | 101835419 | A | * | 9/2010 | A61B 5/02225 |
| CN | 101073496 | B | * | 5/2011 | |
| CN | 105943003 | A | * | 9/2016 | A61B 5/02405 |
| CN | 107536606 | A | | 1/2018 | |
| EP | 2206463 | A1 | * | 7/2010 | A61B 5/02141 |
| JP | H0489029 | A | * | 3/1992 | |
| JP | H1141702 | A | * | 2/1999 | A61B 5/022 |
| JP | H1147102 | A | * | 2/1999 | |
| JP | 2006122144 | A | * | 5/2006 | |
| JP | 2009101089 | A | * | 5/2009 | A61B 5/02141 |
| JP | 5146996 | B2 | * | 2/2013 | A61B 5/0225 |
| JP | 2014-42547 | A | | 3/2014 | |
| JP | 2015-150095 | A | | 8/2015 | |
| JP | 2018-153487 | A | | 10/2018 | |
| JP | 2019-201886 | A | | 11/2019 | |
| TW | 201632139 | A | * | 9/2016 | A61B 5/0235 |

OTHER PUBLICATIONS

Translation of CN 105943003 (Year: 2016).*
Translation of CN 1457743 (Year: 2003).*
Translation of JP 2006122144 (Year: 2006).*
Translation of Feb. 1, 2022 International Search Report issued in International Patent Application No. PCT/JP2021/045149.
Ishizawa et al., "Development of a Novel Algorithm to Detect Atrial Fibrillation Using an Automated Blood Pressure Monitor With an Irregular Heartbeat Detector", Circulation Journal, vol. 83, pp. 2428-2433, Dec. 2019.
Jun. 13, 2025 Office Action issued in Chinese Patent Application No. 202180086188.4.

* cited by examiner

Fig. 5A

RELATED ART

CONVENTIONAL METHOD
SUBJECT : ATRIAL FIBRILLATION PATIENT A

| DATE | TIME | BLOOD PRESSURE/ PULSE RATE (SYS/DIA/PLS) | NUMBER OF TIMES OF IRREGULAR PULSE WAVE OCCURRENCE n | OBJECT DATA AND DETERMINATION RESULT |
|---|---|---|---|---|
| 09/22 | 21:17 | 130/72/66 | 0 | Non-AF |
| 09/22 | 21:18 | 127/70/65 | 0 | |
| 09/22 | 21:19 | 122/67/65 | 0 | |
| 09/23 | 08:39 | 124/78/76 | 5 | AF |
| 09/23 | 08:40 | 120/73/81 | 2 | |
| 09/23 | 08:42 | 122/75/86 | 7 | |
| 09/23 | 16:14 | 117/72/59 | 5 | AF |
| 09/23 | 16:16 | 102/64/62 | 5 | |
| 09/23 | 16:17 | 120/66/62 | 9 | |
| 09/23 | 21:52 | 112/70/61 | 3 | AF |
| 09/23 | 21:53 | 123/67/67 | 10 | |
| 09/23 | 21:55 | 108/67/76 | 5 | |
| : | : | : | : | |

Fig. 5B

PRESENT INVENTION
SUBJECT : ATRIAL FIBRILLATION PATIENT A

| DATE | TIME | BLOOD PRESSURE/ PULSE RATE (SYS/DIA/PLS) | NUMBER OF TIMES OF IRREGULAR PULSE WAVE OCCURRENCE n | OBJECT DATA AND DETERMINATION RESULT |
|---|---|---|---|---|
| 09/22 | 21:17 | 130/72/66 | 0 | D1; AF (rows 09/22 21:17 – 09/23 16:14) |
| 09/23 | 08:39 | 124/78/76 | 5 | D2; AF (rows 09/23 08:39 – 09/23 21:52) |
| 09/23 | 16:14 | 117/72/59 | 5 | |
| 09/23 | 21:52 | 112/70/61 | 3 | |
| : | : | : | : | |

Fig. 6A

RELATED ART

CONVENTIONAL METHOD
SUBJECT : ATRIAL FIBRILLATION PATIENT B

| DATE | TIME | BLOOD PRESSURE/ PULSE RATE (SYS/DIA/PLS) | NUMBER OF TIMES OF IRREGULAR PULSE WAVE OCCURRENCE n | OBJECT DATA AND DETERMINATION RESULT |
|---|---|---|---|---|
| 09/16 | 19:32 | 122/83/ 94 | 6 | AF |
| 09/16 | 19:35 | 122/84/101 | 2 | |
| 09/16 | 19:36 | 120/82/ 93 | 3 | |
| 09/17 | 06:08 | 119/95/ 94 | 3 | INSUFFICIENT NUMBER OF MEASUREMENTS |
| 09/17 | 06:11 | 106/85/ 82 | 4 | |
| 09/17 | 12:49 | 124/91/103 | 2 | AF |
| 09/17 | 12:50 | 113/75/ 91 | 4 | |
| 09/17 | 12:51 | 108/71/101 | 6 | |
| 09/17 | 19:35 | 107/86/110 | 5 | AF |
| 09/17 | 19:36 | 97/70/104 | 3 | |
| 09/17 | 19:37 | 96/71/ 95 | 2 | |
| : | : | : | : | |

Fig. 6B

PRESENT INVENTION
SUBJECT : ATRIAL FIBRILLATION PATIENT B

| DATE | TIME | BLOOD PRESSURE/ PULSE RATE (SYS/DIA/PLS) | NUMBER OF TIMES OF IRREGULAR PULSE WAVE OCCURRENCE n | OBJECT DATA AND DETERMINATION RESULT |
|---|---|---|---|---|
| 09/16 | 19:32 | 122/83/ 94 | 6 | D3; AF (09/16 19:32 – 09/17 12:49) |
| 09/17 | 06:08 | 119/95/94 | 3 | D4; AF (09/17 06:08 – 09/17 19:35) |
| 09/17 | 12:49 | 124/91/103 | 2 | |
| 09/17 | 19:35 | 107/86/110 | 5 | |
| : | : | : | : | |

Fig. 7A

RELATED ART

CONVENTIONAL METHOD
SUBJECT : HEALTHY PERSON C

| DATE | TIME | BLOOD PRESSURE/ PULSE RATE (SYS/DIA/PLS) | NUMBER OF TIMES OF IRREGULAR PULSE WAVE OCCURRENCE n | OBJECT DATA AND DETERMINATION RESULT |
|---|---|---|---|---|
| 08/01 | 04:51 | 104/73/55 | 0 | Non-AF |
| 08/01 | 04:52 | 103/69/54 | 0 | |
| 08/01 | 04:53 | 104/72/53 | 0 | |
| 08/01 | 13:35 | 104/70/75 | 0 | Non-AF |
| 08/01 | 13:36 | 104/70/71 | 0 | |
| 08/01 | 13:37 | 107/69/71 | 0 | |
| 08/01 | 22:53 | 106/71/61 | 0 | Non-AF |
| 08/01 | 22:54 | 103/72/62 | 0 | |
| 08/01 | 22:55 | 103/70/61 | 0 | |
| 08/02 | 05:00 | 111/75/57 | 0 | Non-AF |
| 08/02 | 05:01 | 112/78/55 | 0 | |
| 08/02 | 05:02 | 109/77/53 | 0 | |
| : | : | : | : | |

Fig. 7B

PRESENT INVENTION
SUBJECT : HEALTHY PERSON C

| DATE | TIME | BLOOD PRESSURE/ PULSE RATE (SYS/DIA/PLS) | NUMBER OF TIMES OF IRREGULAR PULSE WAVE OCCURRENCE n | OBJECT DATA AND DETERMINATION RESULT |
|---|---|---|---|---|
| 08/01 | 04:51 | 104/73/55 | 0 | D5; Non-AF (08/01 04:51 – 08/01 22:53) |
| 08/01 | 13:35 | 104/70/75 | 0 | D6; Non-AF (08/01 13:35 – 08/02 05:00) |
| 08/01 | 22:53 | 106/71/61 | 0 | |
| 08/02 | 05:00 | 111/75/57 | 0 | |
| : | : | : | : | |

Fig. 8

PRESENT INVENTION
SUBJECT : ATRIAL FIBRILLATION PATIENT A

| DATE | TIME | BLOOD PRESSURE/ PULSE RATE (SYS/DIA/PLS) | NUMBER OF TIMES OF IRREGULAR PULSE WAVE OCCURRENCE n | OBJECT DATA AND DETERMINATION RESULT |
|---|---|---|---|---|
| 09/17 | 11:10 | 130/80/73 | 0 | D7; OUT OF ALLOWABLE PERIOD |
| 09/20 | 08:36 | 127/76/66 | 0 | |
| 09/21 | 07:40 | 126/68/63 | 1 | |
| : | : | : | : | |
| 9/23 | 08:39 | 124/78/76 | 5 | D8; AF |
| 9/24 | 08:16 | 119/74/78 | 2 | |
| 9/25 | 08:32 | 130/75/63 | 0 | |
| : | : | : | : | |
| : | : | : | : | |

Fig. 12

PRESENT INVENTION
SUBJECT : ATRIAL FIBRILLATION PATIENT A

| DATE | TIME | BLOOD PRESSURE/ PULSE RATE (SYS/DIA/PLS) | NUMBER OF TIMES OF IRREGULAR PULSE WAVE OCCURRENCE n | OBJECT DATA AND DETERMINATION RESULT |
|---|---|---|---|---|
| 09/17 | 11:10 | 130/80/73 | 0 | |
| 09/18 | 21:41 | 133/73/63 | 1 | D9; IRREGULAR PULSE WAVE FREQUENTLY OCCURS |
| 09/19 | 17:09 | 131/74/66 | 1 | |
| : | : | : | : | |
| 9/21 | 07:40 | 126/68/63 | 1 | D10; IRREGULAR PULSE WAVE FREQUENTLY OCCURS |
| 9/22 | 07:50 | 139/80/60 | 0 | |
| 9/23 | 08:39 | 124/78/76 | 5 | |
| 9/24 | 08:16 | 119/74/78 | 2 | |
| 9/25 | 08:32 | 130/75/63 | 0 | |

Fig. 13

PRESENT INVENTION
SUBJECT : ATRIAL FIBRILLATION PATIENT A

| DATE / TIME ZONE | 09/19 | 09/20 | 09/21 | 09/22 | 09/23 | 09/24 | 09/25 |
|---|---|---|---|---|---|---|---|
| MORNING 04:00～10:00 | 08:07<br>124/76/62<br>n=0 | 08:36<br>127/76/66<br>n=0 | 07:40<br>126/68/63<br>n=1 | 07:50<br>139/80/63<br>n=0 | 08:39<br>124/78/76<br>n=5 | 08:16<br>119/74/78<br>n=2 | 08:32<br>130/75/63<br>n=0 |
| DAYTIME 10:00～19:00 | 17:08<br>130/76/65<br>n=0 | 16:21<br>117/69/62<br>n=0 | 16:08<br>108/67/63<br>n=0 | 15:51<br>116/67/65<br>n=0 | 16:14<br>117/72/59<br>n=5 | 15:06<br>110/70/70<br>n=2 | (NO MEASUREMENT) |
| NIGHT 19:00～02:00 | 22:13<br>136/78/68<br>n=0 | (NO MEASUREMENT) | 21:03<br>125/68/62<br>n=1 | 21:17<br>130/72/66<br>n=0 | 21:52<br>112/70/61<br>n=3 | 21:39<br>129/73/66<br>n=0 | (NO MEASUREMENT) |

D12 ; IRREGULAR PULSE WAVE FREQUENTLY OCCURS (MORNING, 09/20–09/24)

D11 ; IRREGULAR PULSE WAVEFREQUENTLY OCCURS (DAYTIME, 09/23–09/24)

ELECTRONIC SPHYGMOMANOMETER AND METHOD FOR DETERMINING ATRIAL FIBRILLATION IN AN ELECTRONIC SPHYGMOMANOMETER

CROSS-REFERENCE TO RELATED APPLICATIONS

This application claims benefit of priority to Japanese Patent Application 2020-212869, filed Dec. 22, 2020, the entire content of which is incorporated herein by reference.

TECHNICAL FIELD

The present invention relates to an electronic sphygmomanometer, and more particularly to an electronic sphygmomanometer capable of determining whether or not there is a possibility that atrial fibrillation occurred. Furthermore, the present invention also relates to an atrial fibrillation determination method in an electronic sphygmomanometer for determining whether or not there is a possibility that atrial fibrillation occurred.

BACKGROUND ART

Conventionally, as an electronic sphygmomanometer for home use, there is an electronic sphygmomanometer equipped with a function of determining whether or not there is a possibility that atrial fibrillation occurred based on acquired pulse wave information (for example, an automatic electronic sphygmomanometer manufactured by OMRON Healthcare Co., Ltd.; M7 Intelli IT). For example, it is assumed that a subject performs blood pressure measurement a plurality of times (for example, three times) consecutively in one measurement occasion using such a sphygmomanometer. Then, pulse wave intervals each of which is an interval between pulse wave signals acquired in each blood pressure measurement are calculated, and each of the pulse wave intervals is compared with an average pulse wave interval in the blood pressure measurement. Then, a pulse wave interval exceeding a preset allowable value such as ±25% is determined to be an irregular pulse wave, and a number of occurrences of the irregular pulse wave is counted. Whether or not there is a possibility that atrial fibrillation occurred is determined according to how many measurement turns occurred in each of which the irregular pulse wave occurred a predetermined number of times or more during a plurality of consecutive blood pressure measurements.

For example. Non Patent Literature 1 (M. Ishizawa et al. "Development of a Novel Algorithm to Detect Atrial Fibrillation Using an Automated Blood Pressure Monitor With an Irregular Heartbeat Detector", Circulation Journal, The Japanese Circulation Society, September 2019, Vol. 83, No. 12, p. 2416-2417) reports a result of determining that there is a possibility that atrial fibrillation occurred in a case where there are two or more measurement turns in each of which the irregular pulse wave occurred one or more times during three consecutive blood pressure measurements. As a result, the sensitivity (a rate at which an atrial fibrillation patient was correctly detected as being atrial fibrillation) is 95.5%, and the specificity (a rate at which a non-atrial fibrillation patient was correctly detected as being non-atrial fibrillation) is 96.5%, which can be very accurately determined.

SUMMARY OF INVENTION

In general, a number of pulses acquired in one blood pressure measurement is around 10 beats. Therefore, it is considered that the determination cannot be made stably in a case where the screening for atrial fibrillation is performed at the number of pulses acquired during one blood pressure measurement.

However, it can be said that it is very troublesome for the subject to always measure the blood pressure three times for every measurement occasion because the total time required for one measurement occasion becomes long and the subject receives a sense of restraint repeatedly pressed by a cuff more than a systolic blood pressure. For example, one blood pressure measurement generally requires a time of about 40 seconds to 60 seconds. Furthermore, it is also recommended that a time interval of 30 seconds to 1 minute be provided between the measurements. Therefore, in order to measure the blood pressure consecutively three times, as illustrated in FIG. 14, a total time of at least 180 seconds (first measurement 40 seconds+interval 30 seconds+second measurement 40 seconds+interval 30 seconds+third measurement 40 seconds) is required.

Therefore, an object of the present invention is to provide an electronic sphygmomanometer, as well as an atrial fibrillation determination method in an electronic sphygmomanometer, that can accurately determine whether or not there is a possibility that atrial fibrillation occurred in a relatively short time per one measurement occasion.

In order to achieve the object, an electronic sphygmomanometer of the present disclosure is an electronic sphygmomanometer that measures blood pressure based on a pulse wave of an artery passing through a site to be measured, the electronic sphygmomanometer comprising:

- a cuff pressure control unit that performs control to pressurize or depressurize a pressure of a cuff worn on the site to be measured;
- a pressure detection unit that detects a cuff pressure signal representing the pressure of the cuff in a pressurization process or a depressurization process by the cuff pressure control unit;
- a blood pressure measurement unit that extracts a pulse wave signal representing a pulse wave superimposed on the cuff pressure signal and measures blood pressure based on the pulse wave signal;
- a pulse wave interval calculation unit that obtains a data group representing pulse wave intervals based on the pulse wave signal obtained only in one pressurization process or one depressurization process for a certain subject for each one measurement occasion; and
- a determination unit that aggregates data groups for three or more measurement occasions of the subject to obtain an average value of the pulse wave intervals, and determines whether or not there is a possibility that atrial fibrillation occurred based on whether or not there is data of an irregular pulse wave exceeding a predetermined allowable range with respect to the average value in the data groups aggregated, wherein
- every time interval between measurement occasions constituting the three measurement occasions is within a predetermined allowable period.

Herein, "one measurement occasion" means an occasion for blood pressure measurement in which a subject wears a cuff once. In the present invention, blood pressure measurement is scheduled to be performed once per one measurement occasion.

Also, "only in one pressurization process or one depressurization process" means that only one blood pressure measurement is performed per one measurement occasion. A number of pieces of data included in one data group is typically assumed to be about 10.

As the “three” measurement occasions, for example, three measurement occasions such as one in the morning, one in the daytime, and one at night on a certain day are assumed, or three measurement occasions such as one in the morning on a certain day, one in the morning on the next day, and one in the morning on the day after next are assumed.

Each of the “pulse wave intervals” means a peak-to-peak interval of a pulse wave (or a bottom-to-bottom interval corresponding thereto).

The “irregular pulse wave” refers to a pulse wave in which the pulse wave interval exceeds a predetermined allowable range with respect to the average value. The “predetermined allowable range” refers to, for example, a range of 25% with respect to the average value. The “predetermined allowable period” means, for example, one day.

In a second aspect, an atrial fibrillation determination method in an electronic sphygmomanometer of the present disclosure is an atrial fibrillation determination method in an electronic sphygmomanometer that measures blood pressure based on a pulse wave of an artery passing through a site to be measured, the electronic sphygmomanometer including:

a cuff pressure control unit that performs control to pressurize or depressurize a pressure of a cuff worn on the site to be measured;

a pressure detection unit that detects a cuff pressure signal representing the pressure of the cuff in a pressurization process or a depressurization process by the cuff pressure control unit; and a blood pressure measurement unit that extracts a pulse wave signal representing a pulse wave superimposed on the cuff pressure signal and measures blood pressure based on the pulse wave signal, the atrial fibrillation determination method comprising:

a step of obtaining a data group representing pulse wave intervals based on the pulse wave signal obtained only in one pressurization process or one depressurization process for a certain subject for each one measurement occasion; and a step of aggregating data groups for three or more measurement occasions of the subject to obtain an average value of the pulse wave intervals, and determining whether or not there is a possibility that atrial fibrillation occurred based on whether or not there is data of an irregular pulse wave exceeding a predetermined allowable range with respect to the average value in the data groups aggregated, wherein every time interval between measurement occasions constituting the three measurement occasions is within a predetermined allowable period.

In a third aspect, an electronic sphygmomanometer of the present disclosure is an electronic sphygmomanometer that measures blood pressure based on a pulse wave of an artery passing through a site to be measured, the electronic sphygmomanometer comprising:

a cuff pressure control unit that performs control to pressurize or depressurize a pressure of a cuff worn on the site to be measured;

a pressure detection unit that detects a cuff pressure signal representing the pressure of the cuff in a pressurization process or a depressurization process by the cuff pressure control unit;

a blood pressure measurement unit that extracts a pulse wave signal representing a pulse wave superimposed on the cuff pressure signal and measures blood pressure based on the pulse wave signal;

a pulse wave interval calculation unit that obtains a data group representing pulse wave intervals based on the pulse wave signal obtained only in one pressurization process or one depressurization process for a certain subject for each one measurement occasion; and a determination unit that aggregates data groups for three or more measurement occasions of the subject to obtain an average value of the pulse wave intervals, and determines whether or not there is a possibility that atrial fibrillation occurred based on whether or not there is data of an irregular pulse wave exceeding a predetermined allowable range with respect to the average value in the data groups aggregated, wherein the electronic sphygmomanometer includes a normal blood pressure measurement mode in which blood pressure measurement is performed only once per one measurement occasion, and an atrial fibrillation screening mode in which blood pressure measurement is repeated three or more times per one measurement occasion, by the cuff pressure control unit, the pressure detection unit, and the blood pressure measurement unit, in the normal blood pressure measurement mode, the determination unit determines whether or not the data of the irregular pulse wave satisfies a predetermined frequent occurrence condition in the data groups aggregated and representing the pulse wave intervals, and the electronic sphygmomanometer includes a notification unit that makes a notification to prompt switching from the normal blood pressure measurement mode to the atrial fibrillation screening mode when the frequent occurrence condition is satisfied.

In a fourth aspect, an electronic sphygmomanometer of the present disclosure is an electronic sphygmomanometer that measures blood pressure based on a pulse wave of an artery passing through a site to be measured, the electronic sphygmomanometer comprising:

a cuff pressure control unit that performs control to pressurize or depressurize a pressure of a cuff worn on the site to be measured;

a pressure detection unit that detects a cuff pressure signal representing the pressure of the cuff in a pressurization process or a depressurization process by the cuff pressure control unit;

a blood pressure measurement unit that extracts a pulse wave signal representing a pulse wave superimposed on the cuff pressure signal and measures blood pressure based on the pulse wave signal;

a pulse wave interval calculation unit that obtains a data group representing pulse wave intervals based on the pulse wave signal obtained only in one pressurization process or one depressurization process for a certain subject for each one measurement occasion; and a determination unit that aggregates data groups for three or more measurement occasions of the subject to obtain an average value of the pulse wave intervals, and determines whether or not there is a possibility that atrial fibrillation occurred based on whether or not there is data of an irregular pulse wave exceeding a predetermined allowable range with respect to the average value in the data groups aggregated, wherein the electronic sphygmomanometer includes a normal blood pressure measurement mode in which blood pressure measurement is performed only once per one measurement occasion, and an atrial fibrillation screening mode in which blood pressure measurement is repeated three or more times per one measurement occasion, by the cuff pressure control unit, the pressure detection unit, and the blood pressure measurement unit, in the normal blood pressure measurement mode, the determination unit determines whether or not the data of the irregular pulse wave satisfies a predetermined frequent occurrence condition in the data groups aggregated and representing the pulse wave intervals, and the electronic sphygmomanometer includes a mode control unit that performs control to switch from the normal blood pressure measurement mode to the atrial fibrillation screening mode when the frequent occurrence condition is satisfied.

BRIEF DESCRIPTION OF DRAWINGS

FIG. 5A is a diagram illustrating object data by a conventional method for a certain subject (atrial fibrillation patient A) and determination results as to whether or not there is a possibility that atrial fibrillation occurred.

FIG. 5B is a diagram illustrating object data according to a first embodiment of the present invention for the subject and determination results as to whether or not there is a possibility that atrial fibrillation occurred.

FIG. 6A is a diagram illustrating object data by the conventional method for another subject (atrial fibrillation patient B) and determination results as to whether or not there is a possibility that atrial fibrillation occurred.

FIG. 6B is a diagram illustrating object data according to the first embodiment for the subject and determination results as to whether or not there is a possibility that atrial fibrillation occurred.

FIG. 7A is a diagram illustrating object data by the conventional method for still another subject (healthy person C) and determination results as to whether or not there is a possibility that atrial fibrillation occurred.

FIG. 7B is a diagram illustrating object data according to the first embodiment for the subject and determination results as to whether or not there is a possibility that atrial fibrillation occurred.

FIG. 8 is a diagram for explaining, using another object data for the subject (atrial fibrillation patient A), how to determine whether or not object data have become available.

FIG. 12 is a diagram illustrating object data according to the flow of FIG. 9A or FIG. 9B for a certain subject (atrial fibrillation patient A) and determination results as to whether or not the frequent occurrence condition is satisfied.

FIG. 13 is a diagram illustrating another object data according to the flow of FIG. 9A or FIG. 9B for the subject (atrial fibrillation patient A) and determination results as to whether or not the frequent occurrence condition is satisfied.

DETAILED DESCRIPTION

Hereinafter, embodiments of the present invention will be described in detail with reference to the drawings.

(Configuration of Sphygmomanometer)

Figure 1:
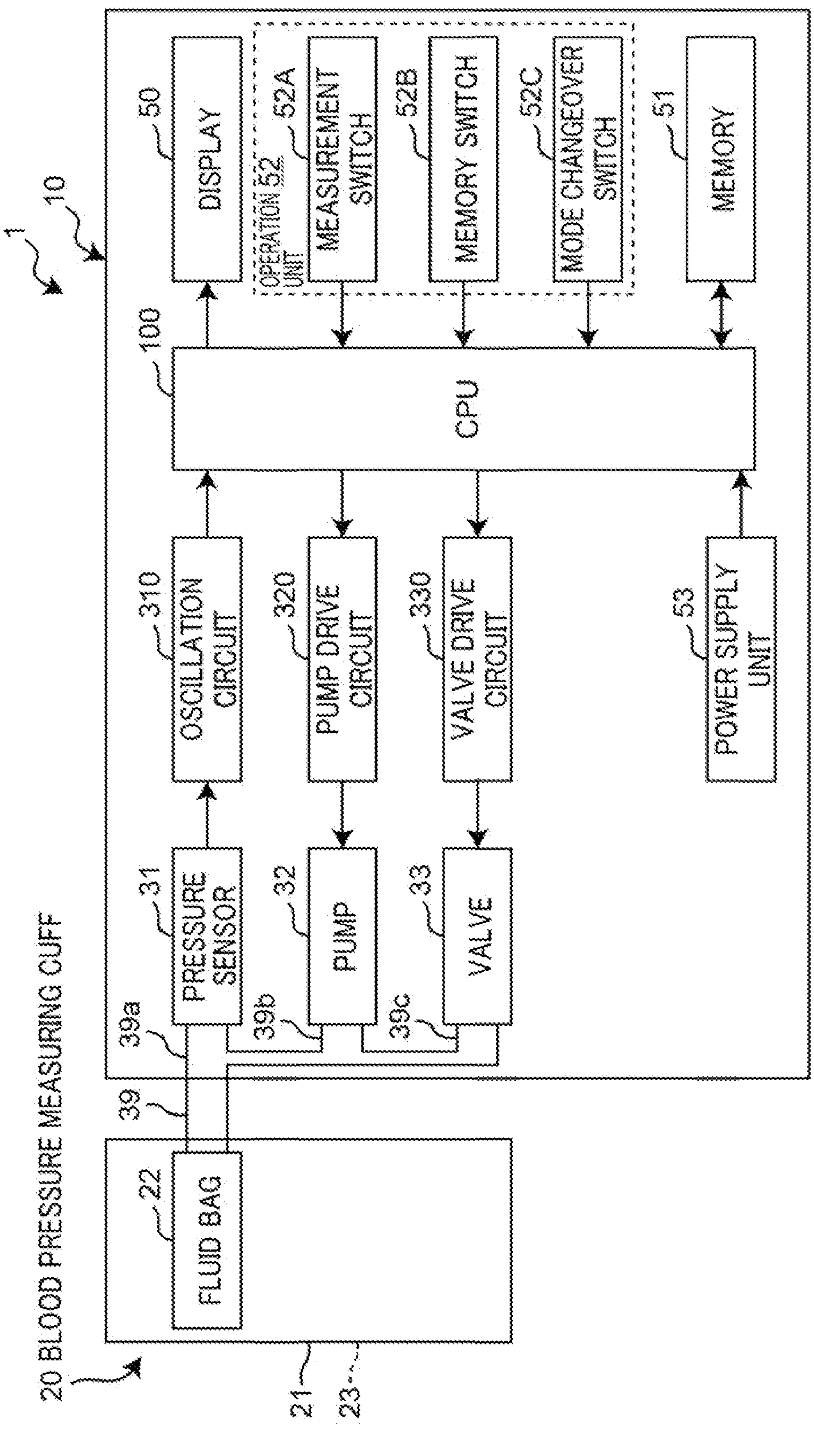
FIG. 1 is a diagram illustrating a block configuration of an electronic sphygmomanometer according to an embodiment of the present invention.

FIG. 1 illustrates a block configuration of an electronic sphygmomanometer 1 according to an embodiment of the present invention. The sphygmomanometer 1 roughly includes a blood pressure measuring cuff 20 worn around a rod-like site to be measured (for example, an upper arm) of a subject, and a main body 10 on which elements for blood pressure measurement are mounted.

The cuff 20 is a general cuff, and is configured by sandwiching a fluid bag 22 between an elongated band-shaped outer cloth 21 and inner cloth 23, and sewing or welding peripheral portions of the outer cloth 21 and the inner cloth 23.

The main body 10 is mounted with a central processing unit (CPU) 100 as a processor, a display 50, an operation unit 52, a memory 51 as a storage unit, a power supply unit 53, a pressure sensor 31, an oscillation circuit 310, a pump 32, a pump drive circuit 320, a valve 33, and a valve drive circuit 330. In this example, an air pipe 39*a* connected to the pressure sensor 31, an air pipe 39*b* connected to the pump 32, and an air pipe 39*c* connected to the valve 33 are joined to form one air pipe 39, and the air pipe 39 is connected to the fluid bag 22 in the cuff 20 so as to be capable of fluid communication. Hereinafter, the air pipes 39*a*, 39*b*, and 39*c* are collectively referred to as the air pipe 39.

Figure 4B:
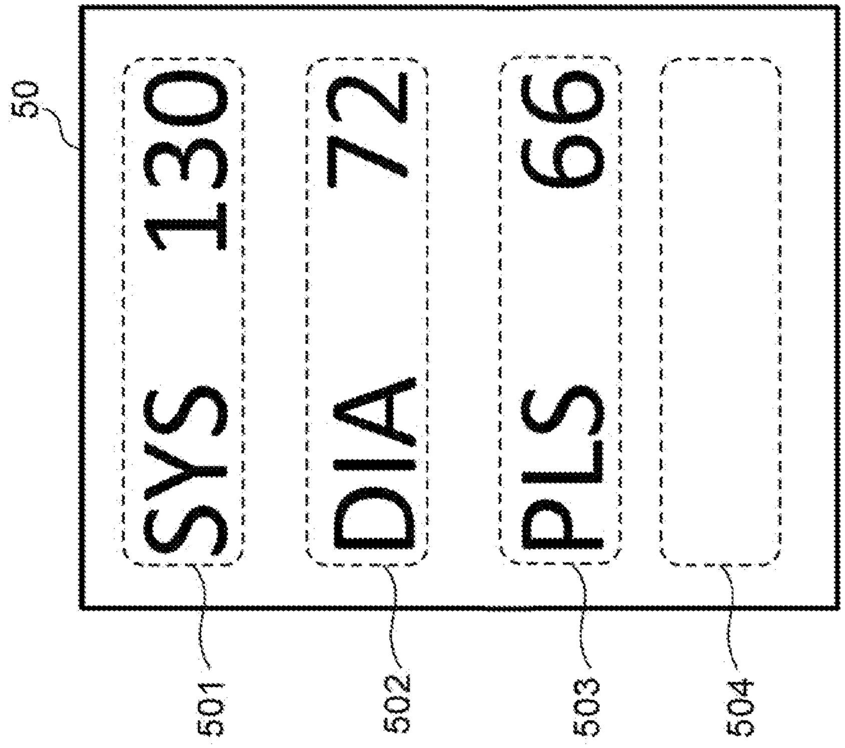
FIG. 4B is a diagram illustrating a displayed screen on the display when there is no possibility that atrial fibrillation occurred (or no information regarding atrial fibrillation) in the normal blood pressure measurement mode.

In this example, the display 50 includes a liquid crystal display (LCD), and displays predetermined information in accordance with a control signal from the CPU 100. In this example, as illustrated in FIG. 4B, the display 50 includes, in order from the top, a SYS display region 501 for displaying a systolic blood pressure SYS (unit; mmHg), a DIA display region 502 for displaying a diastolic blood pressure DIA (unit; mmHg), a PLS display region 503 for displaying a pulse rate PLS (unit; beats/min), and an AF display region 504 for displaying information regarding atrial fibrillation for the subject. Note that, in FIG. 4B, for convenience, each of the display regions 501, 502, 503, and 504 is illustrated by a broken line frame, but the broken line frame is not actually displayed. The display 50 may be an organic electro luminescence (EL) display or may include a light emitting diode (LED).

In this example, the operation unit 52 illustrated in FIG. 1 includes a measurement switch 52A for receiving an instruction to start/stop measurement of blood pressure, a memory switch 52B for calling a recorded result of blood pressure measurement or the like, and a mode changeover switch 52C for receiving an instruction to switch a mode between a normal blood pressure measurement mode and an atrial fibrillation screening mode, and inputs an operation signal according to the user's instruction to the CPU 100.

Here, the "normal blood pressure measurement mode" refers to a mode in which blood pressure measurement is performed only once per one measurement occasion and it is determined whether or not there is a possibility that atrial fibrillation occurred when object data have become available. The "atrial fibrillation screening mode" refers to a mode in which blood pressure measurement is repeated three or more times per one measurement occasion, and it is determined whether or not there is a possibility that atrial fibrillation occurred when object data have become available.

The memory 51 stores data of a program for controlling the sphygmomanometer 1, setting data for setting various functions of the sphygmomanometer 1, data of a measurement result of a blood pressure value, and the like. Furthermore, the memory 51 is used as a work memory or the like when the program is executed.

The CPU 100 controls the operation of the entire sphygmomanometer 1 according to a program for controlling the sphygmomanometer 1 stored in the memory 51. Specific control will be described later.

The pressure sensor 31 is a piezoresistive semiconductor pressure sensor in this example. The pressure sensor 31 outputs a pressure (this is referred to as a "cuff pressure Pc") in the fluid bag 22 contained in the cuff 20 as electric resistance due to the piezoresistive effect through the air pipe 39. The oscillation circuit 310 oscillates at an oscillation frequency corresponding to the electric resistance from the pressure sensor 31. The CPU 100 obtains the cuff pressure Pc according to the oscillation frequency. The pressure sensor 31, the oscillation circuit 310, and the CPU 100 as a whole constitute a pressure detection unit that detects the pressure of the cuff 20. As described later, a pressure fluctuation component (this is referred to as a "pulse wave signal Pm") due to a pulse wave indicated by the site to be measured is superimposed on the cuff pressure Pc.

The pump 32 is driven by the pump drive circuit 320 based on a control signal given from the CPU 100, and supplies air to the fluid bag 22 included in the cuff 20 through the air pipe 39. As a result, the pressure (cuff pressure Pc) of the fluid bag 22 is increased. The valve 33 is a normally-open type electromagnetic valve, is driven by the valve drive circuit 330 based on a control signal given from the CPU 100, and is opened and/or closed to control the cuff pressure Pc by discharging or enclosing the air in the fluid bag 22 through the air pipe 39. The pump 32, the pump drive circuit 320, the valve 33, the valve drive circuit 330, and the CPU 100 as a whole constitute a cuff pressure control unit that performs control to increase or decrease the cuff pressure Pc.

The power supply unit 53 supplies power to the CPU 100, the display 50, the memory 51, the pressure sensor 31, the pump 32, the valve 33, and other units in the main body 10.

First Embodiment

Figure 2A:
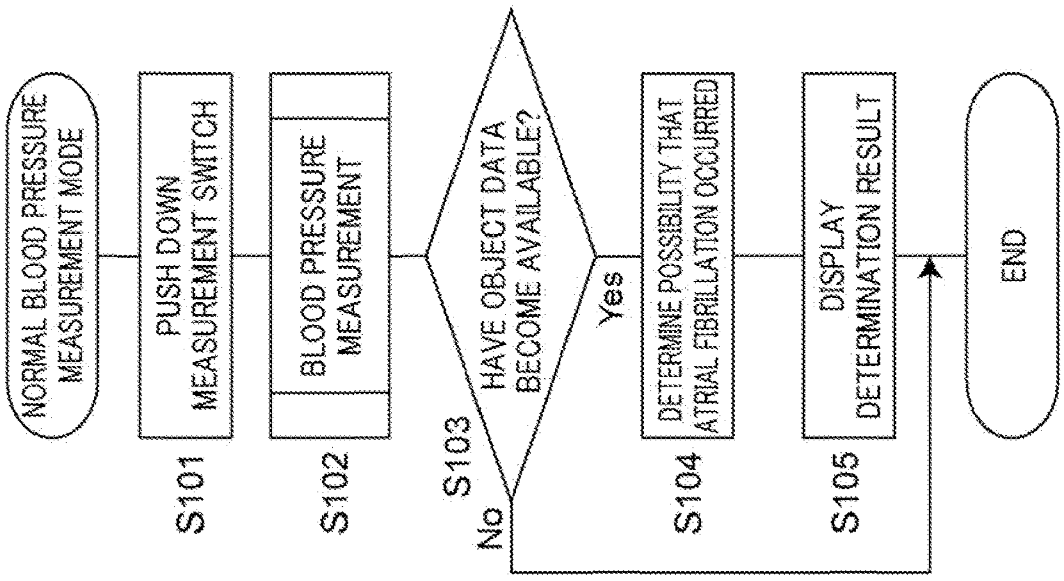
FIG. 2A is a flowchart for determining whether or not there is a possibility that atrial fibrillation occurred in a normal blood pressure measurement mode by the electronic sphygmomanometer.

FIG. 2A illustrates a flow of determining whether or not there is a possibility that atrial fibrillation occurred in the normal blood pressure measurement mode by the CPU 100 of the sphygmomanometer 1. This flow corresponds to processing (including one blood pressure measurement) in one measurement occasion of a certain subject. In this example, once in the morning (04:00 to 10:00), once in the daytime (10:00 to 19:00), and once in the night (19:00 to 02:00) are respectively assumed as the measurement occasion.

When the subject pushes down the measurement switch 52A provided on the main body 10 in a worn state in which the cuff 20 is worn on the site to be measured (step S101 in FIG. 2A), the CPU 100 first executes blood pressure measurement processing (step S102 in FIG. 2A).

Figure 3A:
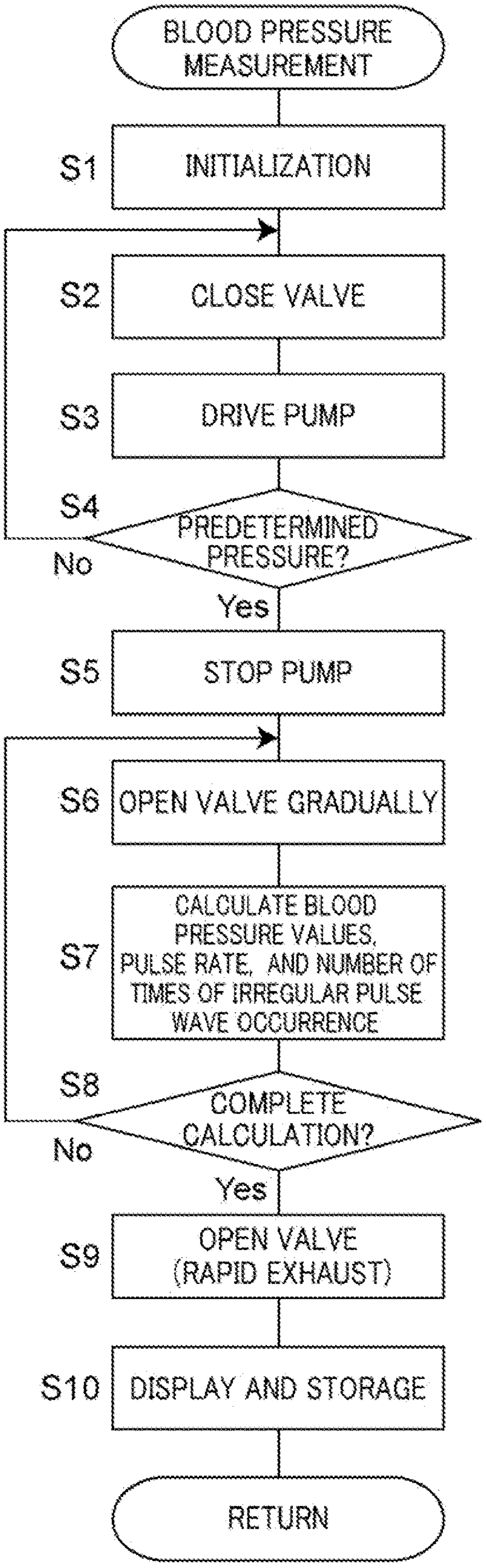
FIG. 3A is a diagram illustrating a flow of blood pressure measurement by the electronic sphygmomanometer.

Specifically, as illustrated in step S1 of FIG. 3A, the CPU 100 first performs initialization. That is, the CPU 100 initializes a processing memory area, stops the pump 32, and performs 0 mmHg adjustment (the atmospheric pressure is set to 0 mmHg) of the pressure sensor 31 in a state where the valve 33 is opened.

Subsequently, the CPU 100 acts, as a pressure control unit, to close the valve 33 (step S2), to drive the pump 32, and to start pressurizing the cuff 20 (step S3). That is, the CPU 100 supplies air from the pump 32 to the fluid bag 22 included in the cuff 20 through the air pipe 39. At the same time, the CPU 100 acts, as a pressure detection unit, to detect the pressure (cuff pressure Pc) in the cuff 20 (fluid bag 22) by the pressure sensor 31 through the air pipe 39, and controls a pressurization speed by the pump 32 based on the cuff pressure Pc. Thereby, the cuff 20 is pressurized, and the artery passing through the site to be measured is compressed. Here, a pressure fluctuation component (pulse wave signal Pm) due to a pulse wave is superimposed on the cuff pressure Pc detected by the pressure sensor 31 in addition to a smoothly changing component (DC component).

Next, when the cuff pressure Pc reaches a predetermined value (in this example, it is set to, for example, 200 mmHg so as to sufficiently exceed an assumed blood pressure value of the subject) (Yes in step S4), the CPU 100 stops the pump 32 (step S5).

Subsequently, the CPU 100 acts as a pressure control unit to gradually open the valve 33 (step S6). Thereby, the cuff pressure Pc is reduced at a substantially constant speed. In a depressurization process, the CPU 100 performs filtering to extract the pulse wave signal Pm from the cuff pressure Pc. Then, in step S7, the CPU 100 acts as a blood pressure measurement unit, and attempts to calculate a blood pressure value (systolic blood pressure (SYS) and diastolic blood pressure (DIA)) by a known oscillometric method based on the pulse wave signal Pm acquired by this time. Furthermore, the CPU 100 calculates a pulse rate PLS [beats/min] based on the pulse wave signal Pm. Moreover, the CPU 100 acts, as a pulse wave interval calculation unit, to obtain a data group representing pulse wave intervals (each of the pulse wave intervals is represented by "$\Delta t$") based on the pulse wave signal Pm for the current measurement occasion (In the first embodiment, a measurement occasion is synonymous with a measurement turn). Furthermore, the CPU 100 acts, as a determination unit, to obtain an average value (this is represented by "Δtave") of the pulse wave intervals for the data group representing the pulse wave intervals Δt, and to determine whether or not data of an irregular pulse wave exists in the data group.

Figure 3B:
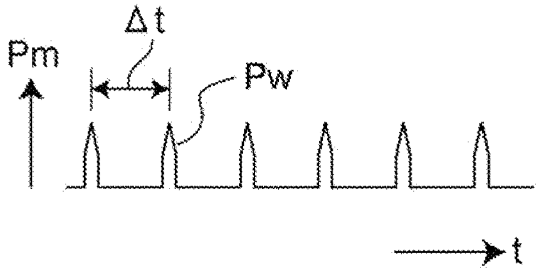
FIG. 3B is a diagram illustrating standard pulse wave intervals.
Figure 3C:
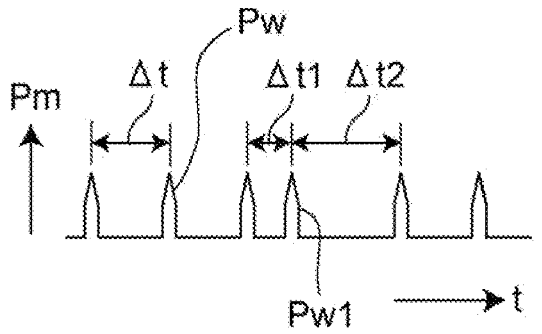
FIG. 3C is a diagram illustrating pulse wave intervals in which an irregular pulse wave occurs.

In this example, as illustrated in FIG. 3B (a graph representing a pulse waveform with a horizontal axis representing time t and a vertical axis representing a pulse wave signal Pm), the pulse wave interval Δt is determined as a peak-to-peak interval between pulse waves Pw. The irregular pulse wave refers to a pulse wave exceeding a predetermined allowable range (in this example, ±25%) with respect to the average value Δtave of the pulse wave intervals. For example, regarding a pulse wave Pw1 illustrated in FIG. 3C, an interval Δt1 between it and a preceding pulse wave or an interval Δt2 between it and a subsequent pulse wave exceeds the allowable range ±25% with respect to the average value Δtave of the pulse wave intervals. Therefore, the pulse wave Pw1 is determined as an irregular pulse wave.

In this example, the CPU 100 calculates, as an individual determination result, a number of times of occurrence of the irregular pulse wave (this is referred to as "the number of times of irregular pulse wave occurrence n") in the data group for the current measurement occasion. When the number of times of irregular pulse wave occurrence n is 0, it indicates that no irregular pulse wave occurred for the current measurement occasion. Furthermore, when the number of times of irregular pulse wave occurrence n is 1 or more, it indicates that the irregular pulse wave occurred in the current measurement occasion.

In a case where the blood pressure values SYS and DIA, the pulse rate PLS, and the number of times of irregular pulse wave occurrence n cannot be calculated yet due to shortage of data (NO in step S8 of FIG. 3A), the CPU 100 repeats the processing of steps S6 to S8 until the blood pressure values SYS and DIA, the pulse rate PLS, and the number of times of irregular pulse wave occurrence n can be calculated.

When the blood pressure values SYS and DIA, the pulse rate PLS, and the number of times of irregular pulse wave occurrence n can be calculated in this manner (Yes in step S8), the CPU 100 acts, as a pressure control unit, to open the valve 33, and to perform control to rapidly exhaust the air in the cuff 20 (fluid bag 22) (step S9).

Thereafter, in step S10 of FIG. 3A, the CPU 100 performs control to display the blood pressure values SYS and DIA and the pulse rate PLS on the display 50. Thereby, as illustrated in FIG. 4B, for example, the systolic blood pressure SYS=130 mmHg, the diastolic blood pressure DIA=72 mmHg, and the pulse rate PLS=66 beats/min are displayed in the SYS display region 501, the DIA display region 502, and the PLS display region 503 in the display 50, respectively. Note that, in step S7 of FIG. 3A, since it has not yet been determined whether there is a possibility that atrial fibrillation occurred, nothing is displayed in the AF display region 504. However, when the current number of times of irregular pulse wave occurrence n for the measurement occasion is 1 or more, a mark, a message, or the like representing that the "irregular pulse wave" occurred may be displayed in the AF display region 504.

Moreover, in step S10 of FIG. 3A, the CPU 100 performs control to store the measurement date and time, the blood pressure values SYS and DIA, the pulse rate PLS, and the number of times of irregular pulse wave occurrence n in the memory 51 in association with each other for the current measurement occasion of the subject. Thereby, as illustrated in FIG. 5B, as a table in the memory 51, the measurement date and time, the blood pressure values SYS and DIA, the pulse rate PLS, and the number of times of irregular pulse wave occurrence n are stored in association with each other for the current measurement occasion of the subject (in this example, atrial fibrillation patient A) in the first row of the table in FIG. 5B (this means row number immediately below a table head. The same applies hereinafter). In this example, the measurement date is 09/22, the measurement time is 21:17, the blood pressure values SYS and DIA and the pulse rate PLS are 130/72/66, and the number of times of irregular pulse wave occurrence n is 0. Note that the units of the blood pressure values SYS and DIA and the pulse rate PLS are not illustrated for simplicity, but as described above, the blood pressure values SYS and DIA are mmHg, and the pulse rate PLS is beat/min (The same applies hereinafter). In this manner, blood pressure measurement is performed once per one measurement occasion. Thereafter, the flow returns to the flow of FIG. 2A.

Note that, in the above example, the blood pressure values, the pulse rate PLS, and the number of times of irregular pulse wave occurrence n are calculated in the depressurization process of the cuff 20 (fluid bag 22), but the present invention is not limited thereto, and the blood pressure values, the pulse rate PLS, and the number of times of irregular pulse wave occurrence n may be calculated in the pressurization process of the cuff 20 (fluid bag 22).

Next, in step S103 of FIG. 2A, the CPU 100 acts, as a determination unit, to search for the individual determination result stored in the memory 51 backward from the latest one (current measurement occasion), and to determine whether or not object data have become available.

Figure 2B:
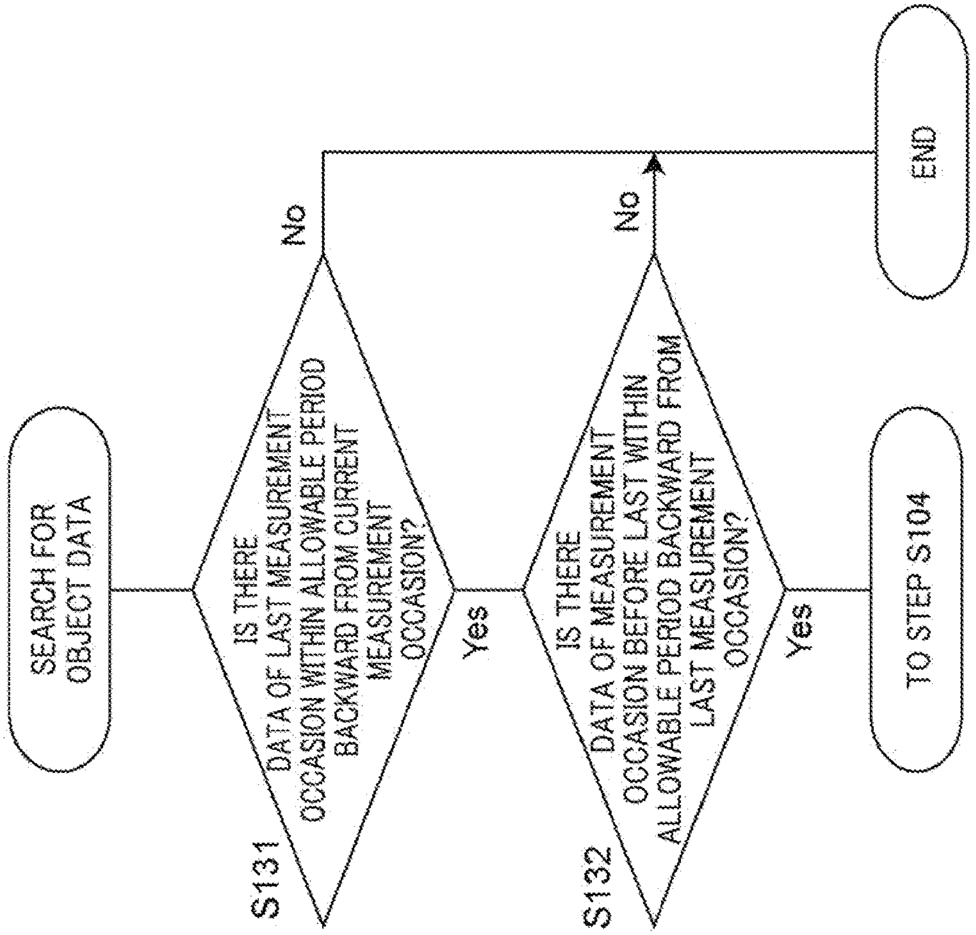
FIG. 2B is a diagram illustrating a flow of processing of searching a memory for object data for determining whether or not there is a possibility that atrial fibrillation occurred in the flow of FIG. 2A.

Specifically, as illustrated in FIG. 2B, it is determined whether or not there is data of the last measurement occasion within an allowable period (in this example, one day) backward from the current measurement occasion (step S131 in FIG. 213). If there is data (Yes in step S131), it is further determined whether or not there is data of the measurement occasion before last within an allowable period (in this example, one day) backward from the last measurement occasion (step S132). When there is no data (No in step S131 or S132), the processing of the normal blood pressure measurement mode is ended.

For example, when the current measurement occasion corresponds to the first row (measurement date: 09/22, measurement time: 21:17) in FIG. 5B and there is no data of the last measurement occasion (No in step S131), the processing of the normal blood pressure measurement mode is ended.

When the subject pushes down the measurement switch 52A provided on the main body 10 in the worn state in which the cuff 20 is worn on the site to be measured in a next measurement occasion (step S101 in FIG. 2A), the CPU 100 starts the blood pressure measurement processing again (step S102 in FIG. 2A). By this blood pressure measurement processing, as illustrated in the second row in FIG. 5B, data is stored in which the measurement date is 09/23, the measurement time is 08:39, the blood pressure values SYS and DIA and the pulse rate PLS are 124/78/76, and the number of times of irregular pulse wave occurrence n is 5. Also in this measurement occasion, since there is no data of the measurement occasion before last (No in step S132), the processing of the normal blood pressure measurement mode is ended.

Moreover, when the subject pushes down the measurement switch 52A provided on the main body 10 in the worn state in which the cuff 20 is worn on the site to be measured in a further next measurement occasion (step S101 of FIG. 2A), the CPU 100 starts the blood pressure measurement processing again (step S102 of FIG. 2A). By this blood pressure measurement processing, as illustrated in the third row in FIG. 5B, data is stored in which the measurement date is 09/23, the measurement time is 16:14, the blood pressure values SYS and DIA and the pulse rate PLS are 117/72/59, and the number of times of irregular pulse wave occurrence n is 5. In this measurement occasion, individual determination results (data of the number of times of irregular pulse wave occurrence n) D1 for three or more measurement occasions are available with satisfying a condition that every time interval between the measurement occasions is within the allowable period (Yes in steps S131 and S132 in FIG. 2B). Therefore, the CPU 100 determines that object data D1 have become available (Yes in step S103 in FIG. 2A). Note that the allowable period may extend over days as long as it is within one day.

At this time, the CPU 100 further acts, as a determination unit, to determine whether or not the individual determination results (the number of times of irregular pulse wave occurrence n) that the irregular pulse wave occurred are obtained for two or more measurement occasions among out of the three measurement occasions (step S104 in FIG. 2A). In the example of FIG. 5B, there is no irregular pulse wave occurrence (the number of times of irregular pulse wave occurrence n=0) for the measurement occasion of the first row (the measurement occasion before last; measurement date: 09/22, measurement time: 21:17), there is irregular pulse wave occurrence (the number of times of irregular pulse wave occurrence n=5) for the measurement occasion of the second row (last measurement occasion; measurement date: 09/23, measurement time: 08:39), and there is irregular pulse wave occurrence (the number of times of irregular pulse wave occurrence n=5) for the measurement occasion of the third row (current measurement occasion; measurement date: 09/23, measurement time: 16:14). In this example, since the irregular pulse wave occurred in two measurement occasions out of the three measurement occasions, it is determined that there is a possibility that atrial fibrillation occurred. For easy understanding, in the rightmost column of FIG. 5B, a range of the object data D1 is illustrated, as well as a determination result "AF" indicating that there is a possibility that atrial fibrillation occurred. Note that a determination result indicating that there is no possibility that atrial fibrillation occurred is represented by "Non-AF".

Figure 4A:
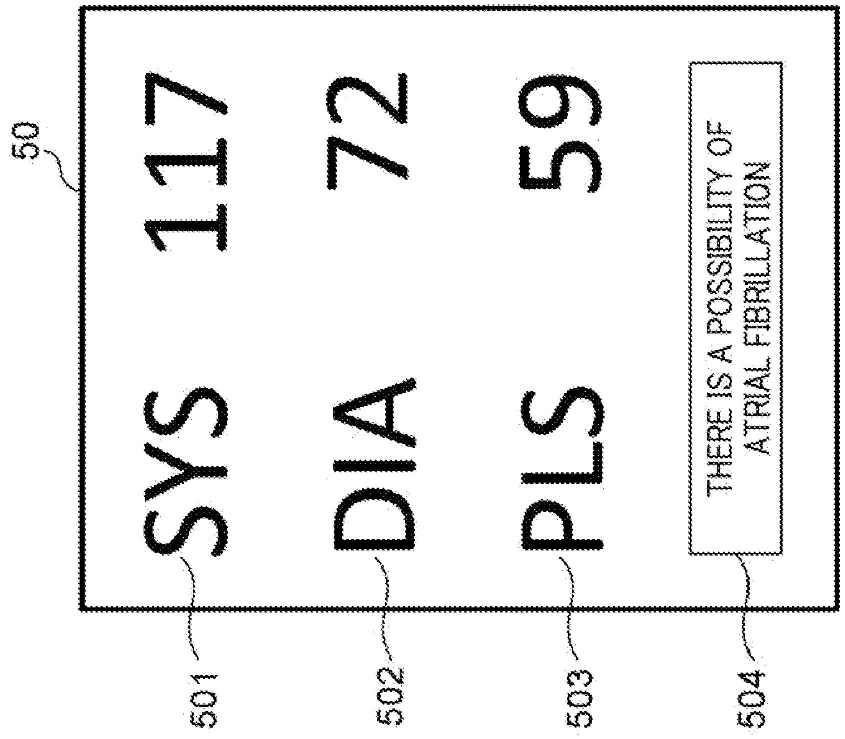
FIG. 4A is a diagram illustrating a displayed screen on a display when it is determined that there is a possibility that atrial fibrillation occurred in the normal blood pressure measurement mode.

Subsequently, the CPU 100 performs control to display, on the display 50, information indicating that there is a possibility that atrial fibrillation occurred, in addition to the current blood pressure values SYS and DIA and the pulse rate PLS for the current measurement occasion. In this example, as illustrated in FIG. 4A, a message "THERE IS A POSSIBILITY OF ATRIAL FIBRILLATION" is displayed in the AF display region 504 of the display 50. Instead of or in addition to the message, a mark indicating that there is a possibility that atrial fibrillation occurred may be displayed.

Thereafter, when the subject pushes down the measurement switch 52A provided on the main body 10 in the worn state in which the cuff 20 is worn on the site to be measured in a further next measurement occasion (step S101 in FIG. 2A), the CPU 100 starts the blood pressure measurement processing again (step S102 in FIG. 2A). By this blood pressure measurement processing, as illustrated in the fourth row in FIG. 5B, data is stored in which the measurement date is 09/23, the measurement time is 21:52, the blood pressure values SYS and DIA and the pulse rate PLS are 112/70/61, and the number of times of irregular pulse wave occurrence n is 3. In this case, in step S103 of FIG. 2A, it is determined that object data D2 illustrated in the second row to the fourth row in FIG. 5B have become available. In this example, since the irregular pulse wave occurred in all the three measurement occasions among the three measurement occasions, it is determined in step S104 of FIG. 2A that there is a possibility that atrial fibrillation occurred.

Thereafter, similarly, it is determined whether or not there is a possibility that atrial fibrillation occurred for each one measurement occasion as long as the subject repeats blood pressure measurement for such measurement occasions of once in the morning, once in the daytime, and once at night.

In this case, a number of pieces of data on which the above determination by the CPU 100 is based is equal to or larger than the number of pieces of data of three consecutive blood pressure measurements in the conventional method. Therefore, according to the sphygmomanometer 1, it is possible to accurately determine whether or not there is a possibility that atrial fibrillation occurred. Furthermore, whether or not there is a possibility that atrial fibrillation occurred can be determined by a simple algorithm.

Furthermore, in the sphygmomanometer 1, in order to determine whether or not there is a possibility that atrial fibrillation occurred, blood pressure measurement only has to be performed once per one measurement occasion, so that the time required per one measurement occasion is relatively short. Note that blood pressure measurement may be performed a plurality of times per one measurement occasion.

Note that, even if the individual determination results (data of the number of times of irregular pulse wave occurrence n) for three or more measurement occasions are obtained in step S103 of FIG. 2A, if any of the time intervals between the measurement occasions is out of the allowable period (No in step S131 or S132 in FIG. 2B, and therefore No in step S103 in FIG. 2A), the CPU 100 does not determine whether there is a possibility that atrial fibrillation occurred, and ends the process of the normal blood pressure measurement mode. For example, in the first row to the third row of the table of FIG. 8, data D7 of individual determination results (the number of times of irregular pulse wave occurrence n) whether or not an irregular pulse wave occurred are obtained for three measurement occasions of the subject. Specifically, there is no irregular pulse wave occurrence (the number of times of irregular pulse wave occurrence n=0) for the measurement occasion of the first row (the measurement occasion before last; measurement date: 09/17, measurement time: 11:10), there is no irregular pulse wave occurrence (the number of times of irregular pulse wave occurrence n=0) for the measurement occasion of the second row (last measurement occasion; measurement date: 09/20, measurement time: 08:36), and there is irregular pulse wave occurrence (the number of times of irregular pulse wave occurrence n=1) for the measurement occasion of the third row (current measurement occasion; measurement date: 09/21, measurement time: 07:40). In this example, since the period from the measurement occasion of the third row (current measurement occasion) to the measurement occasion of the second row (last measurement occasion) is within one day, it is within the allowable period (Yes in step S131 of FIG. 2B). However, since it goes back more than two days from the measurement occasion of the second row (measurement occasion before last) to the measurement occasion of the first row (measurement occasion before last), it is out of the allowable period (No in step S132 in FIG. 2B, and therefore No in step S103 in FIG. 2A). Therefore, the determination as to whether there is a possibility that atrial fibrillation occurred (step S104 in FIG. 2A) is not performed. Note that, in the rightmost column of FIG. 8, it is described that "D7; OUT OF ALLOWABLE PERIOD".

As described above, the old individual determination result (data of the number of times of irregular pulse wave occurrence n) in which the time interval between the measurement occasions exceeds the allowable period is not used as the basis of the determination by the CPU 100. Therefore, reliability of the determination can be improved.

(Comparison and Verification Between Conventional Method and Present Invention)

For example, FIG. 5A illustrates data when the subject (In this example, atrial fibrillation patient A) performed blood pressure measurement consecutively three times per one measurement occasion according to the conventional method. In this example, as illustrated in the first row to the third row of the table of FIG. 5A, blood pressure measurement was consecutively performed three times in one measurement occasion of the 21:00 zone (night) on the measurement date 09/22. In the blood pressure measurement at measurement times 21:17, 21:18, and 21:19, the number of times of irregular pulse wave occurrence n was 0, respectively. In a case where these are used as object data and a determination according to the conventional method (it is determined that there is a possibility that atrial fibrillation occurred when there are two or more measurement turns in each of which the irregular pulse wave occurred one or more times during three consecutive blood pressure measurements) is made, the determination result "Non-AF" indicating that there is no possibility that atrial fibrillation occurred is obtained. Next, as illustrated in the fourth row to the sixth row in FIG. 5A, blood pressure measurement was consecutively performed three times in one measurement occasion of the 8:00 zone (morning) on the measurement date 09/23. In the blood pressure measurement at the measurement times 08:39, 08:40, and 08:42, the irregular pulse wave occurrence number n was 5, 2, and 7, respectively. In a case where these are used as object data and a determination according to the conventional method is made, the determination result "AF" indicating that there is a possibility that atrial fibrillation occurred is obtained. Similarly, the determination result "AF" indicating that there is a possibility that atrial fibrillation occurred is obtained also in one measurement occasion of the 16:00 zone (daytime) on the measurement date 09/23 illustrated in the seventh row to the ninth row in FIG. 5A. Furthermore, in one measurement occasion of the 21:00 zone (night) on measurement date 09/23 illustrated in the 10th row to the 12th row in FIG. 5A, the determination result "AF" indicating that there is a possibility that atrial fibrillation occurred is obtained. As described above, according to the conventional method, since it is determined whether there is a possibility that atrial fibrillation occurred for each one measurement occasion of the subject, even in the data of the atrial fibrillation patient A, the determination results are divided into "Non-AF" and "AF" depending on irregular pulse wave occurrence situation during the measurement occasion. The reason for this is considered that even in the atrial fibrillation patient, the symptoms do not always appear, but the symptoms may appear only temporarily due to environmental factors such as drinking, stress, and shortage of sleep.

The data of the blood pressure values SYS and DIA, the pulse rate PLS, and the number of times of irregular pulse wave occurrence n for the atrial fibrillation patient A in FIG. 5B used for the description of the present invention (first embodiment) correspond to ones extracted from the first time blood pressure measurement among blood pressure measurements for each of the measurement occasions in FIG. 5A. Specifically, the data of the first row (measurement date: 09/22, measurement time: 21:17) among the data in the 21:00 zone (night) on the measurement date 09/22 illustrated in the first row to the third row in FIG. 5A was adopted as the data of the first row in FIG. 5B. Furthermore, the data of the fourth row (measurement date: 09/23, measurement time: 08:39) among the data in the 8:00 zone (morning) on the measurement date 09/23 illustrated in the fourth row to the sixth row in FIG. 5A was adopted as the data of the second row in FIG. 5B. Similarly, the data of the seventh row (Measurement date: 09/23, measurement time: 16:14) among the data in the 16:00 zone (daytime) on the measurement date 09/23 illustrated in the seventh row to the ninth row in FIG. 5A was adopted as the data of the third row in FIG. 5B. Furthermore, the data of the 10th row (measurement date: 09/23, measurement time: 21:52) among the data in the 21:00 zone (night) on the measurement date 09/23 illustrated in the 10th row to the 12th row in FIG. 5A was adopted as the data of the fourth row in FIG. 5B. As described above, according to the first embodiment, in the measurement occasion in which the data of the third row (measurement date: 09/23, measurement time: 16:14) in FIG. 5B is obtained, the object data D1 have become available, and the determination result "AF" indicating that there is a possibility that atrial fibrillation occurred is obtained. Furthermore, in the measurement occasion where the data of the fourth row (measurement date: 09/23, measurement time: 21:52) in FIG. 5B is obtained, the object data D2 have become available, and the determination result "AF" indicating that there is a possibility that atrial fibrillation occurred is obtained. As described above, according to the first embodiment, it is determined that there is a possibility that atrial fibrillation occurred only when individual determination results that the irregular pulse wave occurred are obtained for two or more measurement occasions out of the three measurement occasions. Therefore, it is considered that the dependence on the irregular pulse wave occurrence situation during a specific measurement occasion is alleviated as compared with the conventional method, and as a result, a reasonable (accurate) determination result can be obtained as to whether or not there is a possibility that atrial fibrillation occurred.

FIG. 6A illustrates data when another subject (In this example, atrial fibrillation patient B) performed blood pressure measurement consecutively three times per one measurement occasion according to the conventional method. In this example, as illustrated in the first row to the third row of the table of FIG. 6A, the blood pressure measurement was consecutively performed three times in one measurement occasion of the 19:00 zone (night) on the measurement date 09/16. In the blood pressure measurement at measurement times 19:32, 19:35, and 19:36, the irregular pulse wave occurrence number n was 6, 2, and 3, respectively. In a case where these are used as object data and a determination according to the conventional method (it is determined that there is a possibility that atrial fibrillation occurred when there are two or more measurement turns in each of which the irregular pulse wave occurred one or more times during three consecutive blood pressure measurements) is made, the determination result "AF" indicating that there is a possibility that atrial fibrillation occurred is obtained. Next, as illustrated in the fourth row and the fifth row in FIG. 6A, blood pressure measurement was consecutively performed twice in one measurement occasion of the 6:00 zone (morning) on the measurement date 09/17. In the blood pressure measurement at the measurement times 06:08 and 06:11, the irregular pulse wave occurrence number n was 3 and 4, respectively. In this case, since the blood pressure measurement was stopped at twice, object data have not become available in the conventional method, and thus, the result is "INSUFFICIENT NUMBER OF MEASUREMENTS". Next, as illustrated in the sixth row to the eighth row in FIG. 6A, blood pressure measurement was consecutively performed three times in one measurement occasion of the 12:00 zone (daytime) on the measurement date 09/17. In the blood pressure measurement at measurement times 12:49, 12:50, and 12:51, the irregular pulse wave occurrence number n was 2, 4, and 6, respectively. In a case where these are used as object data and a determination according to the conventional method is made, the determination result "AF" indicating that there is a possibility that atrial fibrillation occurred is obtained. Similarly, the determination result "AF" indicating that there is a possibility that atrial fibrillation occurred is obtained also in one measurement occasion of the 19:00 (night) zone on the measurement date 09/17 illustrated in the ninth row to the 11th row in FIG. 6A. As described above, according to the conventional method, when the blood pressure measurements were less than three times for some reason (erroneous measurement count by subject, failure of sphygmomanometer, etc.) for a certain measurement occasion of the subject, the number of measurements becomes insufficient, and it is not determined whether or not there is a possibility that atrial fibrillation occurred.

The data of the blood pressure values SYS and DIA, the pulse rate PLS, and the number of times of irregular pulse wave occurrence n for the atrial fibrillation patient B illustrated in FIG. 6B correspond to ones extracted, in order to execute the first embodiment of the present invention, from the first time blood pressure measurement among blood pressure measurements for each of the measurement occasions in FIG. 6A, Specifically, the data of the first row (measurement date: 09/16, measurement time: 19:32) among the data in the 19:00 zone (night) on the measurement date 09/16 illustrated in the first row to the third row of the table in FIG. 6A was adopted as the data of the first row of the table in FIG. 6B. Furthermore, the data of the fourth row (measurement date: 09/17, measurement time: 06:08) among the data in the 6:00 zone (morning) on the measurement date 09/17 illustrated in the fourth row and the fifth row in FIG. 6A was adopted as the data of the second row in FIG. 6B. Similarly, the data of the sixth row (measurement date: 09/17, measurement time: 12:49) among the data in the 12:00 zone (daytime) on the measurement date 09/17 illustrated in the sixth row to the eighth row in FIG. 6A was adopted as the data of the third row in FIG. 6B. Furthermore, the data of the ninth row (measurement date: 09/17, measurement time: 19:35) among the data of the 19:00 zone (night) on the measurement date 09/17 illustrated in the ninth row to the 11th row in FIG. 6A was adopted as the data of the fourth row in FIG. 6B. According to the first embodiment, in the measurement occasion where the data of the third row (measurement date: 09/17, measurement time: 12:49) in FIG. 6B is obtained, object data D3 have become available, and the determination result "AF" indicating that there is a possibility that atrial fibrillation occurred is obtained. Furthermore, in the measurement occasion where the data of the fourth row (Measurement date: 09/17, measurement time: 19:35) in FIG. 6B is obtained, object data D4 have become available, and the determination result "AF" indicating that there is a possibility that atrial fibrillation occurred is obtained. As described above, according to the first embodiment, since the data of the blood pressure measurement is performed only once per one measurement occasion, the determination result "AF" indicating that there is a possibility that atrial fibrillation occurred is obtained for each measurement occasion since the measurement occasion (measurement date: 09/17, measurement time: 12:49) of the third row where the object data for the atrial fibrillation patient B have become available. Therefore, according to the first embodiment, since blood pressure measurement only has to be performed once per one measurement occasion where the subject once wears the cuff 20 on the site to be measured, it can be said that the "INSUFFICIENT NUMBER OF MEASUREMENTS" per one measurement occasion is unlikely to occur.

FIG. 7A illustrates data when still another subject (in this example, a healthy person C) performed blood pressure measurement consecutively three times per one measurement occasion according to the conventional method. In this example, as illustrated in the first row to the third row of the table of FIG. 7A, the blood pressure measurement was consecutively performed three times in one measurement occasion of the 4:00 zone (morning) on the measurement date 08/01. In the blood pressure measurement at measurement times 04:51, 04:52, and 04:53, the number of times of irregular pulse wave occurrence n was 0, respectively. In a case where these are used as object data and a determination according to the conventional method is made, the determination result "Non-AF" indicating that there is no possibility that atrial fibrillation occurred is obtained. Next, as illustrated in the fourth row to the sixth row in FIG. 7A, blood pressure measurement was consecutively performed three times in one measurement occasion of the 13:00 zone (daytime) on the measurement date 08/01. In the blood pressure measurement at measurement times 13:35, 13:36, and 13:37, the number of times of irregular pulse wave occurrence n was 0, respectively. In a case where these are used as object data and a determination according to the conventional method is made, the determination result "Non-AF" indicating that there is no possibility that atrial fibrillation occurred is obtained. Similarly, the determination result "Non-AF" indicating that there is no possibility that atrial fibrillation occurred is obtained also for the measurement occasion of the 22:00 zone (night) on the measurement date 08/01 illustrated in the seventh row to the ninth row in FIG. 7A. Furthermore, the result of determination "Non-AF" indicating that there is no possibility that atrial fibrillation occurred is obtained also for the measurement occasion of the 5:00 zone (morning) on the measurement date 08/02 illustrated in the 10th row to the 12th row in FIG. 7A. As described above, according to the conventional method, the determination result "Non-AF" indicating that there is no possibility that atrial fibrillation occurred is obtained for the healthy person C for each one measurement occasion.

The data of the blood pressure values SYS and DIA, the pulse rate PLS, and the number of times of irregular pulse wave occurrence n for the healthy person C illustrated in FIG. 7B correspond to ones extracted, in order to execute the first embodiment of the present invention, from the first time blood pressure measurement among blood pressure measurements for each of the measurement occasions in FIG. 7A, Specifically, the data of the first row (Measurement date: 08/01, measurement time: 04:51) among the data in the 4:00 zone (morning) on the measurement date 08/01 illustrated in the first row to the third row of the table of FIG. 7A was adopted as the data of the first row of the table of FIG. 7B. Furthermore, the data of the fourth row (measurement date: 08/01, measurement time: 13:35) among the data of the 13:00 zone (daytime) on the measurement date 08/01 illustrated in the fourth row to the sixth row in FIG. 7A was adopted as the data of the second row in FIG. 7B. Similarly, the data of the seventh row (measurement date: 08/01, measurement time: 22:53) among the data in the 22:00 zone (night) of the measurement date 08/01 illustrated in the seventh row to the ninth row in FIG. 7A was adopted as the data of the third row in FIG. 7B. Furthermore, the data of the 10th row (measurement date: 08/02, measurement time: 05:00) among the data of the 5:00 zone (morning) on the measurement date 08/02 illustrated in the 10th row to the 12th row in FIG. 7A was adopted as the data of the fourth row in FIG. 7B. According to the first embodiment, in the measurement occasion in which the data of the third row (measurement date: 08/01, measurement time: 22:53) in FIG. 7B is obtained, object data D5 have become available, and the determination result "Non-AF" indicating that there is no possibility that atrial fibrillation occurred is obtained. Furthermore, in the measurement occasion where the data of the fourth row (measurement date: 08/02, measurement time: 05:00) in FIG. 6B is obtained, object data D6 have become available, and the determination result "Non-AF" indicating that there is no possibility that atrial fibrillation occurred is obtained. As described above, according to the first embodiment, the determination result "Non-AF" indicating that there is no possibility that atrial fibrillation occurred is obtained for the healthy person C for each measurement occasion since the measurement occasion (measurement date: 08/01, measurement time: 22:53) of the third row where the object data have become available.

As described above, from the comparison between the determination result of FIG. 5A and the determination result of FIG. 5B, the comparison between the determination result of FIG. 6A and the determination result of FIG. 6B, and the comparison between the determination result of FIG. 7A and the determination result of FIG. 7B, it has been verified that whether or not there is a possibility that atrial fibrillation occurred can be accurately determined according to the first embodiment of the present invention. Furthermore, from the comparison between the determination result of FIG. 6A and the determination result of FIG. 6B, it can be said that in the first embodiment of the present invention, since blood pressure measurement only has to be performed once per one measurement occasion in which the subject once wears the cuff 20 on the site to be measured, it can be said that the "INSUFFICIENT NUMBER OF MEASUREMENTS" per one measurement occasion is unlikely to occur.

The condition that the time interval between the measurement occasions is within the allowable period "one day" is not a strict numerical value, and may be, for example, within one day by rounding off the decimal point (The same applies hereinafter).

Note that, in the above example, one time in the morning (04:00 to 10:00), one time in the daytime (10:00 to 19:00), and one time in the night (19:00 to 02:00) are assumed as the measurement occasion, but the present invention is not limited thereto. For example, as illustrated in the fifth row to the seventh row of the table in FIG. 8, three measurement occasions such as one time in the morning on a certain day, one time in the morning on the next day, and one time in the morning two days later may be assumed. Specifically, a measurement occasion (measurement date 09/23, measurement time 08:39) in the fifth row in FIG. 8 corresponds to one time in the morning on a certain day, wherein a number of times of irregular pulse wave occurrence n is 5. A measurement occasion (measurement date 09/24, measurement time 08:16) in the sixth row corresponds to one time in the morning of the next day, wherein a number of times of irregular pulse wave occurrence n is 2. Furthermore, a measurement occasion on the seventh row (measurement date 09/25, measurement time 08:32) corresponds to one time in the morning two days later, wherein a number of times of irregular pulse wave occurrence n is 0. In this example, in the seventh row of the measurement occasion (measurement date 09/25, measurement time 08:32), object data D8 have become available, and the determination result "AF" indicating that there is a possibility that atrial fibrillation occurred is obtained. As described above, in the first embodiment, three measurement occasions such as one morning on a certain day, one morning on the next day, and one morning on the day after next may be assumed.

Furthermore, in the above example, data groups of the three measurement occasions are used as the object data, but the present invention is not limited thereto. Data groups of four or more measurement occasions may be used as the object data.

Furthermore, in the above example, in step S7 of FIG. 3A, the individual determination result (the number of times of irregular pulse wave occurrence n) representing whether or not the irregular pulse wave occurred is obtained for each one measurement occasion, but the present invention is not limited thereto. An average value of pulse wave intervals may be obtained by collectively aggregating data groups representing pulse wave intervals of three or more measurement occasions of the subject, and whether there is a possibility that atrial fibrillation occurred may be determined based on whether or not data of the irregular pulse wave exceeding a predetermined allowable range with respect to the average value exist in the collectively aggregated data groups.

Second Embodiment

Figure 9A:
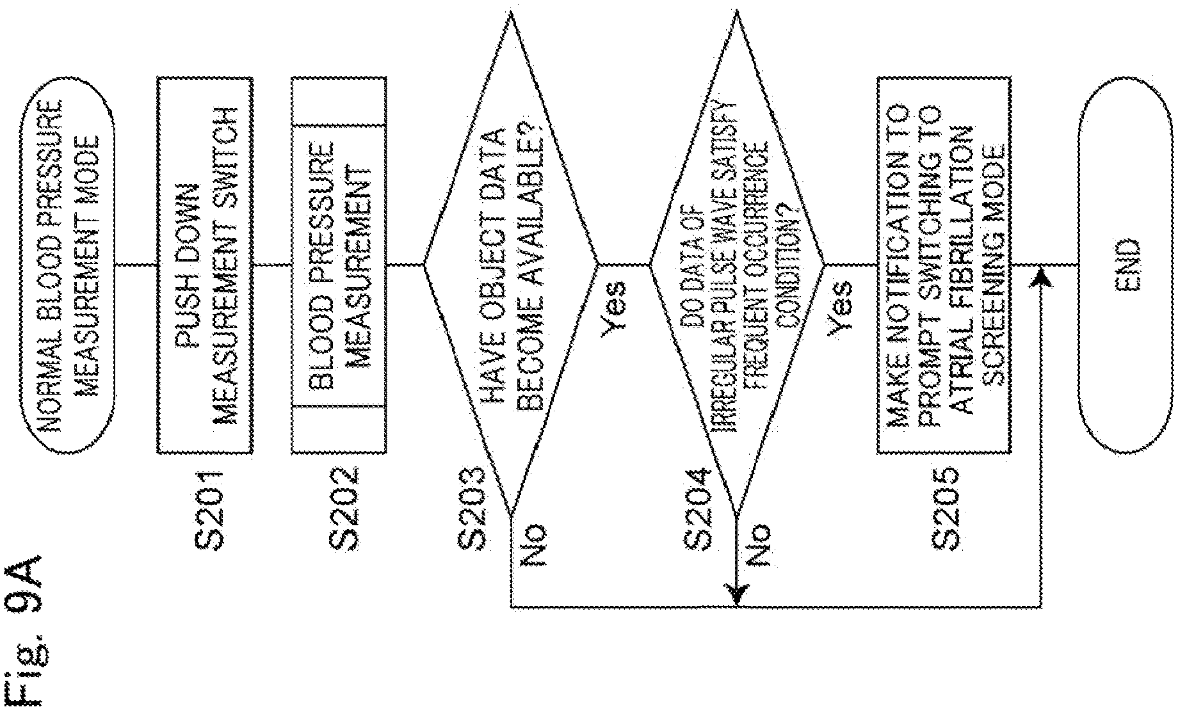
FIG. 9A is a diagram illustrating a flow of determining whether or not data of an irregular pulse wave for a subject satisfies a predetermined frequent occurrence condition in the normal blood pressure measurement mode.

FIG. 9A illustrates a flow of determining whether or not the data of the irregular pulse wave for the subject satisfies a predetermined frequent occurrence condition in the normal blood pressure measurement mode.

The "predetermined frequent occurrence condition" includes:

i) a condition that one or more pieces of data of the irregular pulse wave existed in each of the data groups representing the pulse wave intervals for the latest two measurement occasions;

ii) a condition that one or more pieces of data of the irregular pulse wave existed in each of a majority of the data groups (that is, data groups for three or more measurement occasions) representing the pulse wave intervals for the latest five measurement occasions;

iii) a condition that one or more pieces of data of the irregular pulse wave existed in each of the data groups representing the pulse wave intervals for the latest two measurement occasions in the same time zone (morning, daytime, night, etc.) of every day; and iv) a condition that one or more pieces of data of the irregular pulse wave existed in each of a majority of the data groups (that is, data groups for three or more measurement occasions) representing the pulse wave intervals for the latest five measurement occasions in the same time zone (morning, daytime, night, etc.) of every day.

In a case where the frequent occurrence condition of the above i) or iii) is set, it is necessary that individual determination results (data of the number of times of irregular pulse wave occurrence n) for two measurement occasions within the allowable period have become available as object data. In a case where the frequent occurrence condition of the above ii) or iv) is set, it is necessary that individual determination results for five measurement occasions within the allowable period have become available as object data. In this manner, how many individual determination results of measurement occasions need to be available as the object data is determined according to the predetermined frequent occurrence condition.

In the first example, it is assumed that the frequent occurrence condition is the above i), i.e., the "condition that one or more pieces of data of the irregular pulse wave existed in each of the data groups for the latest two measurement occasions."

When the subject (In this example, atrial fibrillation patient A) pushes down the measurement switch 52A provided on the main body 10 in the worn state in which the cuff 20 is worn on the site to be measured (step S201 in FIG. 9A), the CPU 100 first executes blood pressure measurement processing (step S202 in FIG. 9A). In step S202, similarly as in step S102 in FIG. 2A, the CPU 100 acts, as a determination unit, to calculate the number of times of irregular pulse wave occurrence n as an individual determination result in the data group for the current measurement occasion (In the second embodiment, the measurement occasion has the same meaning as the measurement turn only in the normal blood pressure measurement mode).

Here, for example, it is assumed that the data of the first row and the second row of the table of FIG. 12 has already been stored, and the data of the current measurement occasion has been stored in the third row of the table of FIG. 12. Specifically, in the measurement occasion of the first row (measurement occasion before last; measurement date 09/17, measurement time 11:10) in FIG. 12, the number of times of irregular pulse wave occurrence n is 0. In the measurement occasion of the second row (last measurement occasion; measurement date 09/18, measurement time 21:41), the number of times of irregular pulse wave occurrence n is 1. In the measurement occasion of the third row (current measurement occasion; measurement date 09/19, measurement time 17:09), the number of times of irregular pulse wave occurrence n is 1.

Next, in step S203 in FIG. 9A, the CPU 100 searches for the individual determination result stored in the memory 51 backward from the latest one (current measurement occasion), and determines whether object data have become available. In the second row and the third row of the example in FIG. 12, individual determination results (data of the number of times of irregular pulse wave occurrence n) for two measurement occasions are obtained. Therefore, the CPU 100 determines that object data D9 have become available (Yes in step S203 of FIG. 9A). Note that, when the object data have not yet become available (No in step S203), the processing is ended and a next measurement occasion is waited.

In a case where the object data have become available, in step S204 of FIG. 9A, the CPU 100 acts, as a determination unit, to determine whether or not the data of the irregular pulse wave satisfies a predetermined frequent occurrence condition. In the second row and the third row of the example in FIG. 12, the number of times of irregular pulse wave occurrence n is 1 or more in each of the last measurement occasion (measurement date 09/18, measurement time 21:41) and the current measurement occasion (measurement date 09/19, measurement time 17:09). Therefore, the CPU 100 determines that the "condition that one or more pieces of data of irregular pulse wave existed in each of the data groups representing the pulse wave intervals for the latest two measurement occasions." of the above i) is satisfied (Yes in step S204 in FIG. 9A). For easy understanding, in the rightmost column of FIG. 12, a range of the object data D9 is illustrated, as well as a determination result "IRREGULAR PULSE WAVE FREQUENTLY OCCURS" indicating that the frequent occurrence condition is satisfied. Note that, when the frequent occurrence condition is not satisfied (No in step S204), the processing is ended, and a next measurement occasion is waited.

Figure 11A:
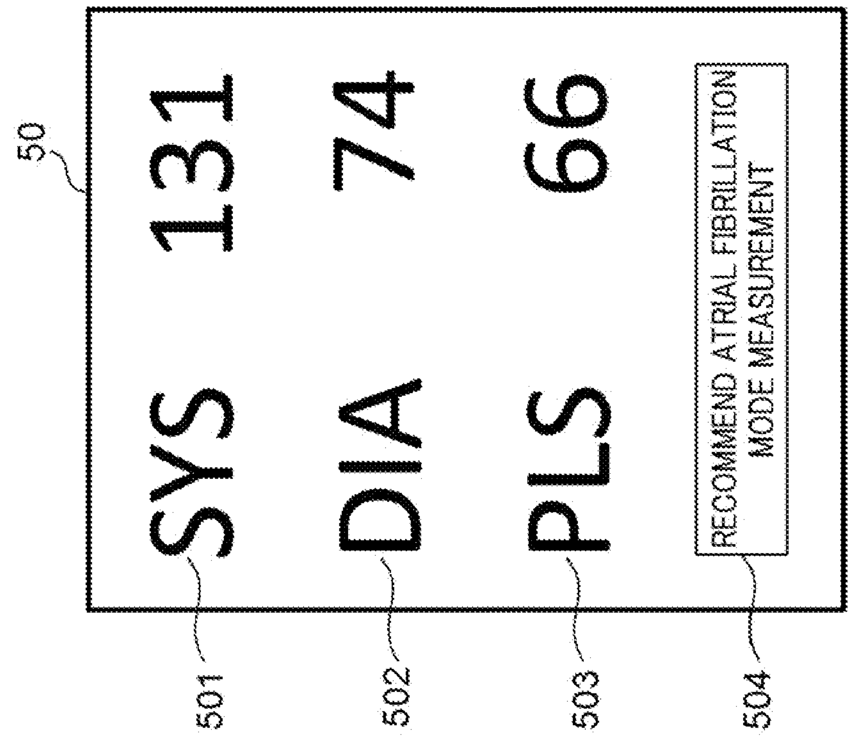
FIG. 11A is a diagram illustrating a displayed screen on the display when it is determined that the frequent occurrence condition is satisfied by the flow of FIG. 9A.

When the frequent occurrence condition is satisfied, in step S205 in FIG. 9A, the CPU 100 acts, as a notification unit, to make a notification to prompt switching from the normal blood pressure measurement mode to the atrial fibrillation screening mode. For example, as illustrated in FIG. 11A, a message "RECOMMEND ATRIAL FIBRILLATION MODE MEASUREMENT" is displayed in the AF display region 504 of the display 50. By this notification, the user (including the subject and medical staffs such as a doctor and a nurse) is urged to switch from the normal blood pressure measurement mode to the atrial fibrillation screening mode (described later). When the user switches to the atrial fibrillation screening mode by the mode changeover switch 52C (see FIG. 1), a screening for atrial fibrillation is performed more accurately than in the normal blood pressure measurement mode. Note that, instead of or in addition to the message, a mark prompting switching to the atrial fibrillation screening mode may be displayed.

Figure 9B:
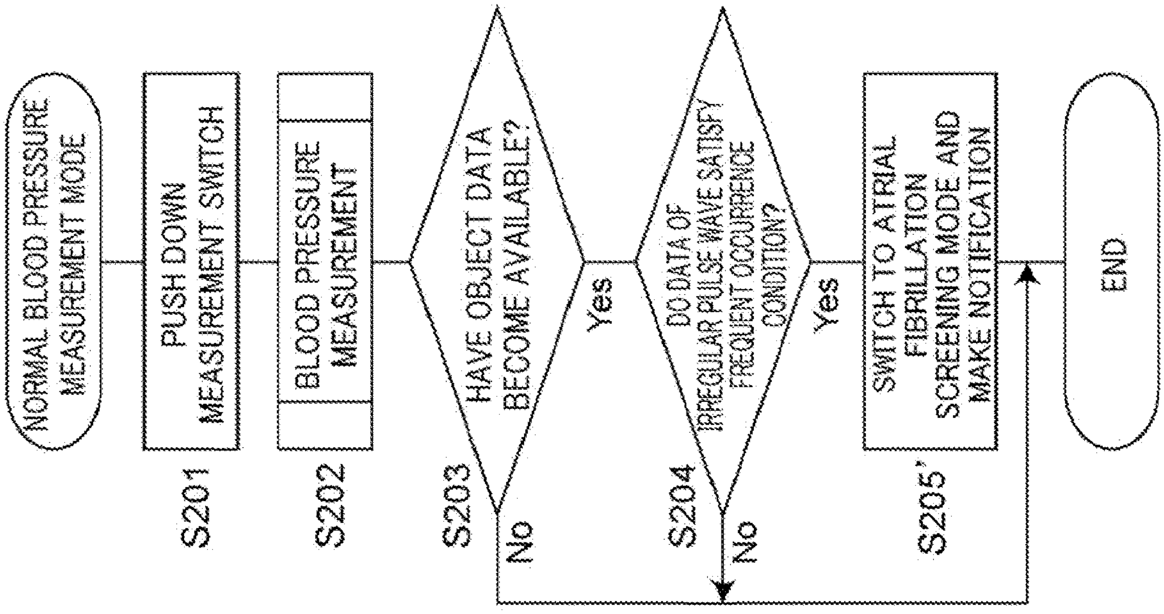
FIG. 9B is a diagram illustrating another flow of determining whether or not data of an irregular pulse wave for the subject satisfies a predetermined frequent occurrence condition in the normal blood pressure measurement mode.
Figure 11B:
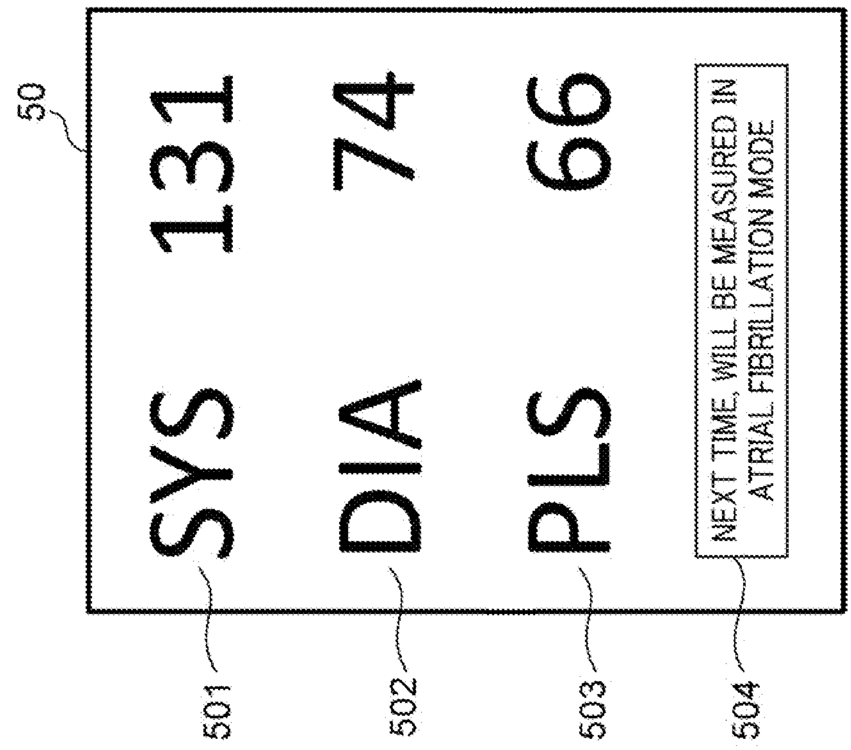
FIG. 11B is a diagram illustrating a displayed screen on the display when it is determined that the frequent occurrence condition is satisfied by the flow of FIG. 9B.
Figure 14:
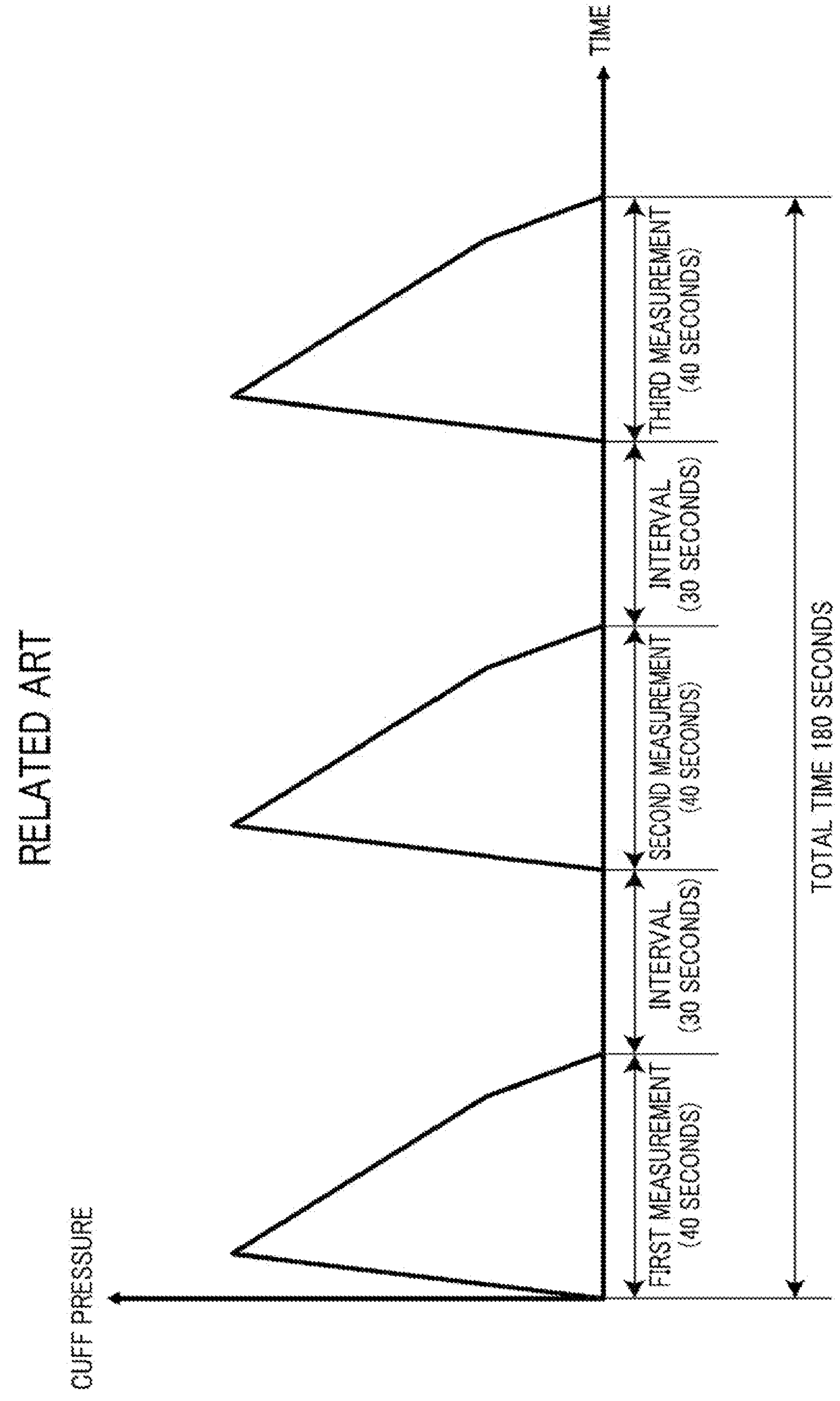
FIG. 14 is a diagram illustrating a total time required per one measurement occasion in a case where it is determined whether or not there is a possibility that atrial fibrillation occurred by a conventional method.

Alternatively, as illustrated in step S205' in FIG. 9B, the CPU 100 may act as a mode control unit to perform control to switch from the normal blood pressure measurement mode to the atrial fibrillation screening mode. In this case, for example, as illustrated in FIG. 11B, a message "NEXT TIME, WILL BE MEASURED IN ATRIAL FIBRILLATION MODE" is displayed in the AF display region 504 of the display 50. Note that steps S201 to S204 in FIG. 9B are the same as steps S201 to S204 in FIG. 9A.

Figure 10:
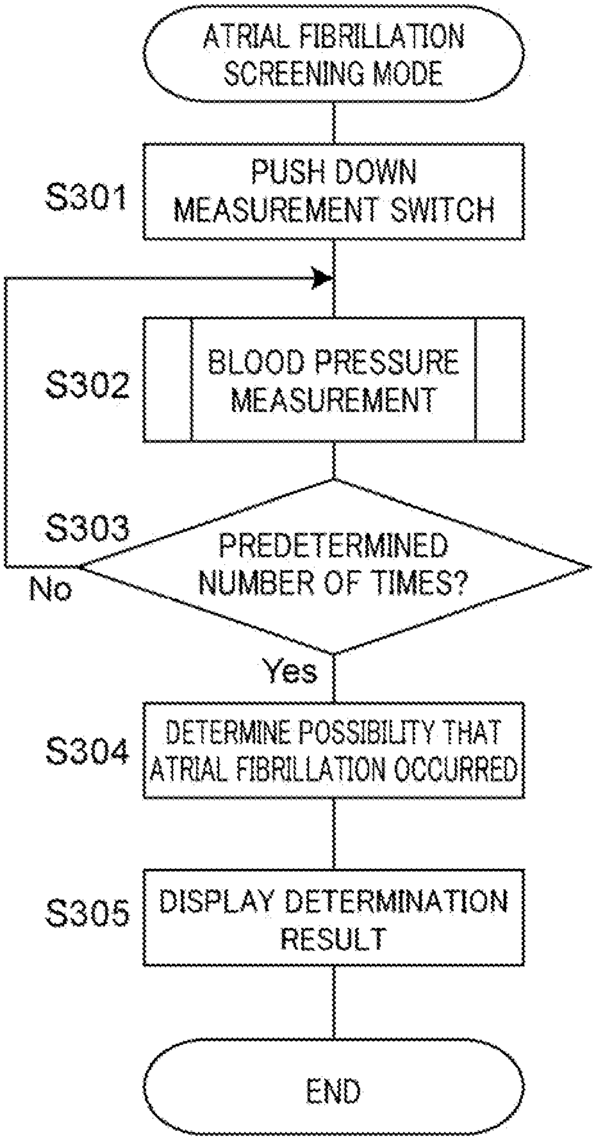
FIG. 10 is a diagram illustrating a flow of an atrial fibrillation screening mode by the electronic sphygmomanometer.

FIG. 10 illustrates a flow of the atrial fibrillation screening mode by the CPU 100 of the sphygmomanometer 1. In the atrial fibrillation screening mode, it is scheduled to repeat blood pressure measurement three or more times per one measurement occasion.

When the subject pushes down the measurement switch 52A provided on the main body 10 in the worn state in which the cuff 20 is worn on the site to be measured (step S301 in FIG. 10), the CPU 100 starts the processing of the atrial fibrillation screening mode.

In the atrial fibrillation screening mode, the CPU 100 first executes blood pressure measurement processing (step S302 in FIG. 10). Step S302 is the same as step S202 in FIG. 9A or 9B (Specifically, steps S1 to S10 in FIG. 3A). Thereby, the measurement date and time, the blood pressure values SYS and DIA, the pulse rate PLS, and the number of times of irregular pulse wave occurrence n are associated with each other and stored in the memory 51 for the current measurement performed by the subject at the current measurement occasion.

Next, as illustrated in step S303 of FIG. 10, the CPU 100 determines whether the blood pressure measurement (step S302) has been performed a predetermined number of times (In this example, three times). If the blood pressure measurement has not been performed the predetermined number of times (No in step S303), the process is repeated until it is completed. Thereby, data (that is, the measurement date and time of the blood pressure measurement, the blood pressure values SYS and DIA, the pulse rate PLS, and the number of irregular pulse wave occurrences n) of three consecutive blood pressure measurements for the current measurement occasion are stored in the memory 51.

Next, as illustrated in step S304 of FIG. 10, the CPU 100 determines whether or not there is a possibility that atrial fibrillation occurred, for example, by a conventional method, using the data of three consecutive blood pressure measurements stored in the memory 51 as object data. Specifically, it is determined that there is a possibility that atrial fibrillation occurred in a case where there are two or more measurement turns in each of which the irregular pulse wave occurred one or more times during three consecutive blood pressure measurements. When a number of measurement turn in which the irregular pulse wave occurred one or more times is one or less, it is determined that there is no possibility that atrial fibrillation occurred.

Next, as illustrated in step S305 of FIG. 10, in addition to the blood pressure values SYS and DIA and the pulse rate PLS of the last measurement, the CPU 100 performs control to display information indicating that there is a possibility that atrial fibrillation occurred on the display 50. For example, similarly to the display in the AF display region 504 in FIG. 4A, a message "THERE IS A POSSIBILITY OF ATRIAL FIBRILLATION" is displayed. Note that, instead of or in addition to the message, a mark prompting switching to the atrial fibrillation screening mode may be displayed.

As described above, in the atrial fibrillation screening mode, blood pressure measurement is repeated three or more times per one measurement occasion. Therefore, in the atrial fibrillation screening mode, it is possible to more accurately determine whether or not there is a possibility that atrial fibrillation occurred, as compared with the normal blood pressure measurement mode.

Note that, in the example of FIG. 10, data groups of three consecutive blood pressure measurements for the current measurement occasion are used as the object data, but the present invention is not limited thereto. Data groups of four or more measurement occasions may be used as the object data.

Modified Example 1

An example in which the above ii), i.e., the "condition that one or more pieces of data of the irregular pulse wave existed in each of a majority of the data groups (that is, data groups for three or more measurement occasions) representing the pulse wave intervals for the latest five measurement occasions" is adopted as the frequent occurrence condition will be described.

When attention is paid to the fifth row to the ninth row of the table of FIG. 12, the number of times of irregular pulse wave occurrence n is 1 in the measurement occasion (measurement date 09/21, measurement time 07:40) of the fifth row. In the measurement occasion of the sixth row (measurement date 09/22, measurement time 07:50), the number of times of irregular pulse wave occurrence n is 0. In the measurement occasion of the seventh row (measurement date 09/23, measurement time 08:39), the number of times of irregular pulse wave occurrence n is 5. In the measurement occasion of the eighth row (measurement date 09/24, measurement time 08:16), the number of times of irregular pulse wave occurrence n is 2. In the measurement occasion of the ninth row (current measurement occasion; measurement date 09/25, measurement time 08:32), the number of times of irregular pulse wave occurrence n is 0.

In this case, when data of the measurement occasion (current measurement occasion) of the ninth row in FIG. 12 is obtained, the CPU 100 determines that object data D10 have become available (Yes in step S203 of FIG. 9A). Then, in step S204 of FIG. 9A, the CPU 100 acts as a determination unit to determine whether or not the data of the irregular pulse wave satisfies the frequent occurrence condition of the above ii). In the example of the fifth row to the ninth row in FIG. 12, the number of times of irregular pulse wave occurrence n is 1 or more in each of the three measurement occasions, i.e., the measurement occasion of the fifth row (measurement date 09/21, measurement time 07:40), the measurement occasion of the seventh row (measurement date 09/23, measurement time 08:39), and the measurement occasion of the eighth row (measurement date 09/24, measurement time 08:16). Therefore, the CPU 100 determines that the "condition that one or more pieces of data of the irregular pulse wave existed in each of a majority of the data groups (that is, data groups for three or more measurement occasions) representing the pulse wave intervals for the latest five measurement occasions" of the above ii) is satisfied (Yes in step S204 in FIG. 9A). For easy understanding, in the rightmost column of FIG. 12, a range of the object data D10 is illustrated, as well as a determination result "IRREGULAR PULSE WAVE FREQUENTLY OCCURS" indicating that the frequent occurrence condition is satisfied. After this determination, as described above, the processing of step S205 of FIG. 9A or step S205' of FIG. 9B continues.

Modified Example 2

An example in which the above iii), i.e., the "condition that one or more pieces of data of the irregular pulse wave existed in each of the data groups representing the pulse wave intervals for the latest two measurement occasions in the same time zone (morning, daytime, night, etc.) of every day" is adopted as the frequent occurrence condition will be described.

In the table of FIG. 13, the measurement dates 09/19, 09/20, . . . , and 09/25 are indicated on the table head, and the measurement time zones of "MORNING (04:00 to 10:00)", "DAYTIME (10:00 to 19:00)", and "NIGHT (19:00 to 02:00)" are indicated on the table side. In each frame in the table body, the measurement time (for example, in the upper left corner frame, 08:07), the values of the blood pressure values SYS and DIA and the pulse rate PLS (for example, in the upper left corner frame, 124/76/62) obtained at the measurement time, and the number of times of irregular pulse wave occurrence n (for example, in the upper left corner frame, n=0) are displayed in order from the top. In this example, in FIG. 13, attention is paid to a measurement occasion (measurement date 09/23, measurement time 16:14) in the daytime time zone on the measurement date 09/23 and a measurement occasion (measurement date 09/24, measurement time 15:06) in the daytime time zone on the measurement date 09/24. It is assumed that the latter measurement occasion (measurement date 09/24, measurement time 15:06) is the current measurement occasion.

In this case, when data of the measurement occasion (measurement date 09/24, measurement time 15:06) in the daytime time zone of the measurement date 09/24 is obtained, the CPU 100 determines that object data D11 have become available (Yes in step S203 of FIG. 9A). Then, in step S204 of FIG. 9A, the CPU 100 acts as a determination unit to determine whether or not the data of the irregular pulse wave satisfies the frequent occurrence condition of the above iii). In the above example, the number of times of irregular pulse wave occurrence n is 1 or more in both the measurement occasion (measurement date 09/23, measurement time 16:14) in the daytime time zone on the measurement date 09/23 and the measurement occasion (measurement date 09/23, measurement time 15:06) in the daytime time zone on the measurement date 09/24. Therefore, the CPU 100 determines that the "condition that one or more pieces of data of the irregular pulse wave existed in each of the data groups representing the pulse wave intervals for the latest two measurement occasions in the same time zone (morning, daytime, night, etc.) of every day" of the above iii) is satisfied (Yes in step S204 in FIG. 9A). For easy understanding, in the field of the daytime time zone in FIG. 13, a range of the object data D11 is illustrated, as well as a determination result "IRREGULAR PULSE WAVE FREQUENTLY OCCURS" indicating that the frequent occurrence condition is satisfied. After this determination, as described above, the processing of step S205 of FIG. 9A or step S205' of FIG. 9B continues.

Modified Example 3

An example in which the above iv), i.e., the "condition that one or more pieces of data of the irregular pulse wave existed in each of a majority of the data groups (that is, data groups for three or more measurement occasions) representing the pulse wave intervals for the latest five measurement occasions in the same time zone (morning, daytime, night, etc.) of every day" is adopted as the frequent occurrence condition will be described.

In this example, in FIG. 13, attention is paid to a measurement occasion (measurement date 09/20, measurement time 08:36) in the morning time zone of the measurement date 09/20, a measurement occasion (measurement date 09/21, measurement time 07:40) in the morning time zone of the measurement date 09/21, a measurement occasion (measurement date 09/22, measurement time 07:50) in the morning time zone of the measurement date 09/22, a measurement occasion (measurement date 09/23, measurement time 08:39) in the morning time zone of the measurement date 09/23, and a measurement occasion (measurement date 09/24, measurement time 08:16) in the morning time zone of the measurement date 09/24. It is assumed that the measurement occasion (measurement date 09/24, measurement time 08:16) in the morning time zone of the measurement date 09/24 is the current measurement occasion.

In this case, when the data of the measurement occasion (measurement date 09/24, measurement time 08:16) in the morning time zone of the measurement date 09/24 is obtained, the CPU 100 determines that object data D12 have become available (Yes in step S203 of FIG. 9A). Then, in step S204 of FIG. 9A, the CPU 100 acts as a determination unit to determine whether or not the data of the irregular pulse wave satisfies the frequent occurrence condition of the above iv). In the above example, the number of times of irregular pulse wave occurrence n is 1 or more in each of the three measurement occasions, i.e., the measurement occasion (measurement date 09/21, measurement time 07:40) in the morning time zone of the measurement date 09/21, the measurement occasion (measurement date 09/23, measurement time 08:39) in the morning time zone of the measurement date 09/23, and the measurement occasion (measurement date 09/24, measurement time 08:16) in the morning time zone of the measurement date 09/24. Therefore, the CPU 100 determines that the "condition that one or more pieces of data of the irregular pulse wave existed in each of a majority of the data groups (that is, data groups for three or more measurement occasions) representing the pulse wave intervals for the latest five measurement occasions in the same time zone (morning, daytime, night, etc.) of every day" of the above iv) is satisfied (Yes in step S204 in FIG. 9A). For easy understanding, in the field of the morning time zone in FIG. 13, a range of the object data D12 is illustrated, as well as a determination result "IRREGULAR PULSE WAVE FREQUENTLY OCCURS" indicating that the frequent occurrence condition is satisfied. After this determination, as described above, the processing of step S205 of FIG. 9A or step S205' of FIG. 9B continues.

Note that the frequent occurrence conditions i) to iv) described above may be employed alone, or alternatively, they may be used in combination at the same time. In the case of the combined use, when any of the frequent occurrence conditions i) to iv) described above is satisfied in the current measurement occasion, the CPU 100 determines that the data of the irregular pulse wave satisfies the frequent occurrence condition (Yes in step S204 in FIG. 9A). Thereby, it is possible to accurately determine whether or not the irregular pulse wave frequently occurs.

Furthermore, the "predetermined frequent occurrence condition" in the second embodiment may be the condition itself, as described in the first embodiment, that, with measurement being performed once per one measurement occasion, the irregular pulse wave occurred (the number of times of irregular pulse wave occurrence n is 1 or more) in two or more measurement occasions out of the three measurement occasions. In other words, the condition may be that one or more pieces of data of the irregular pulse wave existed in the data groups representing the pulse wave intervals for two or more measurement occasions among the three measurement occasions.

In the above example, the site to be measured is the upper arm, but the present invention is not limited thereto. The site to be measured may be an upper limb other than the upper arm such as a wrist or a lower limb such as an ankle.

In the above example, the atrial fibrillation determination method according to the present invention is applied to a sphygmomanometer that performs blood pressure measurement by oscillometric method. However, the present invention is not limited thereto, and the atrial fibrillation determination method according to the present invention can be applied to various types of electronic sphygmomanometers such as a sphygmomanometer that performs blood pressure measurement by tonometry (A method in which a blood vessel is pressed from above the skin so as to be partially flattened, and blood pressure is continuously measured for each beat based on a pulse wave signal).

As described above, an electronic sphygmomanometer of the present disclosure is an electronic sphygmomanometer that measures blood pressure based on a pulse wave of an artery passing through a site to be measured, the electronic sphygmomanometer comprising:

a cuff pressure control unit that performs control to pressurize or depressurize a pressure of a cuff worn on the site to be measured;

a pressure detection unit that detects a cuff pressure signal representing the pressure of the cuff in a pressurization process or a depressurization process by the cuff pressure control unit;

a blood pressure measurement unit that extracts a pulse wave signal representing a pulse wave superimposed on the cuff pressure signal and measures blood pressure based on the pulse wave signal;

a pulse wave interval calculation unit that obtains a data group representing pulse wave intervals based on the pulse wave signal obtained only in one pressurization process or one depressurization process for a certain subject for each one measurement occasion; and a determination unit that aggregates data groups for three or more measurement occasions of the subject to obtain an average value of the pulse wave intervals, and determines whether or not there is a possibility that atrial fibrillation occurred based on whether or not there is data of an irregular pulse wave exceeding a predetermined allowable range with respect to the average value in the data groups aggregated, wherein every time interval between measurement occasions constituting the three measurement occasions is within a predetermined allowable period.

Herein, "one measurement occasion" means an occasion for blood pressure measurement in which a subject wears a cuff once. In the present invention, blood pressure measurement is scheduled to be performed once per one measurement occasion.

Also, "only in one pressurization process or one depressurization process" means that only one blood pressure measurement is performed per one measurement occasion. A number of pieces of data included in one data group is typically assumed to be about 10.

As the "three" measurement occasions, for example, three measurement occasions such as one in the morning, one in the daytime, and one at night on a certain day are assumed, or three measurement occasions such as one in the morning on a certain day, one in the morning on the next day, and one in the morning on the day after next are assumed.

Each of the "pulse wave intervals" means a peak-to-peak interval of a pulse wave (or a bottom-to-bottom interval corresponding thereto).

The "irregular pulse wave" refers to a pulse wave in which the pulse wave interval exceeds a predetermined allowable range with respect to the average value. The "predetermined allowable range" refers to, for example, a range of 25% with respect to the average value. The "predetermined allowable period" means, for example, one day.

In the electronic sphygmomanometer of the present disclosure, the blood pressure is measured as follows based on a pulse wave of an artery passing through the site to be measured. First, it is assumed that a subject wears a cuff on a site to be measured and meets a measurement occasion. The cuff pressure control unit places a pressure of the cuff worn on the site to be measured in a pressurization process or a depressurization process. In the pressurization process or the depressurization process by the cuff pressure control unit, the pressure detection unit detects a cuff pressure signal representing the pressure of the cuff. The blood pressure measurement unit extracts a pulse wave signal representing a pulse wave superimposed on the cuff pressure signal, and measures blood pressure based on the pulse wave signal. In this manner, blood pressure measurement is performed once per one measurement occasion.

Here, the pulse wave interval calculation unit obtains a data group representing pulse wave intervals on the basis of the pulse wave signal obtained only in one pressurization process or one depressurization process for a certain subject for each one measurement occasion. A number of pieces of data included in one data group is typically assumed to be about 10. As described above, it is considered that whether or not there is a possibility that atrial fibrillation occurred cannot be accurately determined with the number of pieces of data of about 10. Therefore, in this electronic sphygmomanometer, the determination unit aggregates data groups for three or more measurement occasions of the subject to obtain an average value of the pulse wave intervals, and determines whether or not there is a possibility that atrial fibrillation occurred based on whether or not there is data of an irregular pulse wave exceeding a predetermined allowable range with respect to the average value in the data groups aggregated. In this case, the number of pieces of data on which the above determination is based is equal to or larger than the number of pieces of data of three consecutive blood pressure measurements in the conventional method (Refers to the method of consecutively measuring blood pressure three times per one measurement occasion described in Non Patent Literature 1. The same applies hereinafter). Therefore, according to this electronic sphygmomanometer, it is possible to accurately determine whether or not there is a possibility that atrial fibrillation occurred. In the electronic sphygmomanometer, particularly, since every time interval between measurement occasions constituting the three measurement occasions is within the predetermined allowable period, reliability of the determination can be improved.

Furthermore, in this electronic sphygmomanometer, blood pressure measurement only has to be performed once per one measurement occasion in order to determine whether or not there is a possibility that atrial fibrillation occurred, so that the time required per one measurement occasion is relatively short. Note that blood pressure measurement may be performed a plurality of times per one measurement occasion.

In the electronic sphygmomanometer according to one embodiment, the determination unit obtains an average value of the pulse wave intervals for each data group for each one measurement occasion, determines whether or not there is the data of the irregular pulse wave in the data group, and obtains an individual determination result representing whether or not the irregular pulse wave occurred for each one measurement occasion, and determines that there is a possibility that atrial fibrillation occurred only when individual determination results that the irregular pulse wave occurred are obtained for two or more measurement occasions out of the three measurement occasions.

In the electronic sphygmomanometer according to this one embodiment, the determination unit obtains an average value of the pulse wave intervals for each of the data groups for each one measurement occasion, determines whether or not there is the data of the irregular pulse wave in the data group, and obtains an individual determination result as to whether or not the irregular pulse wave occurred for each one measurement occasion. Moreover, the determination unit determines that there is a possibility that atrial fibrillation occurred only when individual determination results that the irregular pulse wave occurred are obtained for two or more measurement occasions out of the three measurement occasions. Thus, whether or not there is a possibility that atrial fibrillation occurred can be determined by a simple algorithm.

The electronic sphygmomanometer according to one embodiment further comprises a storage unit that stores the individual determination result for each one measurement occasion in association with a measurement date and time, wherein the determination unit searches for the individual determination result stored in the storage unit backward from the latest one, and determines whether or not there is a possibility that atrial fibrillation occurred only when the individual determination results for the three or more measurement occasions are available with satisfying a condition that every time interval between the measurement occasions is within the allowable period.

In the electronic sphygmomanometer of this one embodiment, the storage unit stores the individual determination result for each one measurement occasion in association with the measurement date and time. The determination unit searches for the individual determination result stored in the storage unit backward from the latest one, and determines whether or not there is a possibility that atrial fibrillation occurred only when the individual determination results for the three or more measurement occasions are available with satisfying a condition that every time interval between the measurement occasions is within the allowable period. Conversely, an old individual determination result in which the time interval between the measurement occasions exceeds the allowable period is not used as a basis of determination by the determination unit. Therefore, reliability of the determination can be improved.

In the electronic sphygmomanometer according to one embodiment, the electronic sphygmomanometer includes a normal blood pressure measurement mode in which blood pressure measurement is performed only once per one measurement occasion, and an atrial fibrillation screening mode in which blood pressure measurement is repeated three or more times per one measurement occasion, by the cuff pressure control unit, the pressure detection unit, and the blood pressure measurement unit, in the normal blood pressure measurement mode, the determination unit determines whether or not the data of the irregular pulse wave satisfies a predetermined frequent occurrence condition in the data groups aggregated and representing the pulse wave intervals, and the electronic sphygmomanometer includes a notification unit that makes a notification to prompt switching from the normal blood pressure measurement mode to the atrial fibrillation screening mode when the frequent occurrence condition is satisfied.

The "predetermined frequent occurrence condition" includes:

i) a condition that one or more pieces of data of the irregular pulse wave existed in each of the data groups representing the pulse wave intervals for the latest two measurement occasions;

ii) a condition that one or more pieces of data of the irregular pulse wave existed in each of a majority of the data groups (that is, data groups for three or more measurement occasions) representing the pulse wave intervals for the latest five measurement occasions;

iii) a condition that one or more pieces of data of the irregular pulse wave existed in each of the data groups representing the pulse wave intervals for the latest two measurement occasions in the same time zone (morning, daytime, night, etc.) of every day; and iv) a condition that one or more pieces of data of the irregular pulse wave existed in each of a majority of the data groups (that is, data groups for three or more measurement occasions) representing the pulse wave intervals for the latest five measurement occasions in the same time zone (morning, daytime, night, etc.) of every day.

In this embodiment, the electronic sphygmomanometer is, by default, in a normal blood pressure measurement mode in which blood pressure measurement is performed only once per one measurement occasion by the cuff pressure control unit, the pressure detection unit, and the blood pressure measurement unit. In the normal blood pressure measurement mode, the determination unit determines whether or not the data of the irregular pulse wave satisfies a predetermined frequent occurrence condition in the data groups aggregated and representing the pulse wave intervals. When the frequent occurrence condition is satisfied, the notification unit makes a notification to prompt switching from the normal blood pressure measurement mode to the atrial fibrillation screening mode. By this notification, a user (including the subject and medical staffs such as a doctor and a nurse. The same applies hereinafter) is prompted to switch from the normal blood pressure measurement mode to the atrial fibrillation screening mode. When the mode is switched to the atrial fibrillation screening mode, the screening for atrial fibrillation can be performed more accurately than in the normal blood pressure measurement mode.

In the electronic sphygmomanometer according to one embodiment, the electronic sphygmomanometer includes a normal blood pressure measurement mode in which blood pressure measurement is performed only once per one measurement occasion, and an atrial fibrillation screening mode in which blood pressure measurement is repeated three or more times per one measurement occasion, by the cuff pressure control unit, the pressure detection unit, and the blood pressure measurement unit, in the normal blood pressure measurement mode, the determination unit determines whether or not the data of the irregular pulse wave satisfies a predetermined frequent occurrence condition in the data groups aggregated and representing the pulse wave intervals, and the electronic sphygmomanometer includes a mode control unit that performs control to switch from the normal blood pressure measurement mode to the atrial fibrillation screening mode when the frequent occurrence condition is satisfied.

In this embodiment, the electronic sphygmomanometer is, by default, in a normal blood pressure measurement mode in which blood pressure measurement is performed only once per one measurement occasion by the cuff pressure control unit, the pressure detection unit, and the blood pressure measurement unit. In the normal blood pressure measurement mode, the determination unit determines whether or not the data of the irregular pulse wave satisfies a predetermined frequent occurrence condition in the data groups aggregated and representing the pulse wave intervals. When the frequent occurrence condition is satisfied, the mode control unit performs control to switch from the normal blood pressure measurement mode to the atrial fibrillation screening mode. In the atrial fibrillation screening mode, blood pressure measurement is repeated three or more times per one measurement occasion. Therefore, in the atrial fibrillation screening mode, it is possible to more accurately determine whether or not there is a possibility that atrial fibrillation occurred, as compared with the normal blood pressure measurement mode.

In a second aspect, an atrial fibrillation determination method in an electronic sphygmomanometer of the present disclosure is an atrial fibrillation determination method in an electronic sphygmomanometer that measures blood pressure based on a pulse wave of an artery passing through a site to be measured, the electronic sphygmomanometer including:

a cuff pressure control unit that performs control to pressurize or depressurize a pressure of a cuff worn on the site to be measured;

a pressure detection unit that detects a cuff pressure signal representing the pressure of the cuff in a pressurization process or a depressurization process by the cuff pressure control unit; and a blood pressure measurement unit that extracts a pulse wave signal representing a pulse wave superimposed on the cuff pressure signal and measures blood pressure based on the pulse wave signal, the atrial fibrillation determination method comprising:

a step of obtaining a data group representing pulse wave intervals based on the pulse wave signal obtained only in one pressurization process or one depressurization process for a certain subject for each one measurement occasion; and a step of aggregating data groups for three or more measurement occasions of the subject to obtain an average value of the pulse wave intervals, and determining whether or not there is a possibility that atrial fibrillation occurred based on whether or not there is data of an irregular pulse wave exceeding a predetermined allowable range with respect to the average value in the data groups aggregated, wherein every time interval between measurement occasions constituting the three measurement occasions is within a predetermined allowable period.

According to the atrial fibrillation determination method in an electronic sphygmomanometer of the present disclosure, it is possible to accurately determine whether or not there is a possibility that atrial fibrillation occurred. Particularly, since every time interval between measurement occasions constituting the three measurement occasions is within the predetermined allowable period, reliability of the determination can be improved. Furthermore, in order to determine whether or not there is a possibility that atrial fibrillation occurred, blood pressure measurement only has to be performed once per one measurement occasion, so that the time required per one measurement occasion is relatively short.

In a third aspect, an electronic sphygmomanometer of the present disclosure is an electronic sphygmomanometer that measures blood pressure based on a pulse wave of an artery passing through a site to be measured, the electronic sphygmomanometer comprising:

a cuff pressure control unit that performs control to pressurize or depressurize a pressure of a cuff worn on the site to be measured;

a pressure detection unit that detects a cuff pressure signal representing the pressure of the cuff in a pressurization process or a depressurization process by the cuff pressure control unit;

a blood pressure measurement unit that extracts a pulse wave signal representing a pulse wave superimposed on the cuff pressure signal and measures blood pressure based on the pulse wave signal;

a pulse wave interval calculation unit that obtains a data group representing pulse wave intervals based on the pulse wave signal obtained only in one pressurization process or one depressurization process for a certain subject for each one measurement occasion; and a determination unit that aggregates data groups for three or more measurement occasions of the subject to obtain an average value of the pulse wave intervals, and determines whether or not there is a possibility that atrial fibrillation occurred based on whether or not there is data of an irregular pulse wave exceeding a predetermined allowable range with respect to the average value in the data groups aggregated, wherein the electronic sphygmomanometer includes a normal blood pressure measurement mode in which blood pressure measurement is performed only once per one measurement occasion, and an atrial fibrillation screening mode in which blood pressure measurement is repeated three or more times per one measurement occasion, by the cuff pressure control unit, the pressure detection unit, and the blood pressure measurement unit, in the normal blood pressure measurement mode, the determination unit determines whether or not the data of the irregular pulse wave satisfies a predetermined frequent occurrence condition in the data groups aggregated and representing the pulse wave intervals, and the electronic sphygmomanometer includes a notification unit that makes a notification to prompt switching from the normal blood pressure measurement mode to the atrial fibrillation screening mode when the frequent occurrence condition is satisfied.

In a fourth aspect, an electronic sphygmomanometer of the present disclosure is an electronic sphygmomanometer that measures blood pressure based on a pulse wave of an artery passing through a site to be measured, the electronic sphygmomanometer comprising:

a cuff pressure control unit that performs control to pressurize or depressurize a pressure of a cuff worn on the site to be measured;

a pressure detection unit that detects a cuff pressure signal representing the pressure of the cuff in a pressurization process or a depressurization process by the cuff pressure control unit;

a blood pressure measurement unit that extracts a pulse wave signal representing a pulse wave superimposed on the cuff pressure signal and measures blood pressure based on the pulse wave signal;

a pulse wave interval calculation unit that obtains a data group representing pulse wave intervals based on the pulse wave signal obtained only in one pressurization process or one depressurization process for a certain subject for each one measurement occasion; and a determination unit that aggregates data groups for three or more measurement occasions of the subject to obtain an average value of the pulse wave intervals, and determines whether or not there is a possibility that atrial fibrillation occurred based on whether or not there is data of an irregular pulse wave exceeding a predetermined allowable range with respect to the average value in the data groups aggregated, wherein the electronic sphygmomanometer includes a normal blood pressure measurement mode in which blood pressure measurement is performed only once per one measurement occasion, and an atrial fibrillation screening mode in which blood pressure measurement is repeated three or more times per one measurement occasion, by the cuff pressure control unit, the pressure detection unit, and the blood pressure measurement unit, in the normal blood pressure measurement mode, the determination unit determines whether or not the data of the irregular pulse wave satisfies a predetermined frequent occurrence condition in the data groups aggregated and representing the pulse wave intervals, and the electronic sphygmomanometer includes a mode control unit that performs control to switch from the normal blood pressure measurement mode to the atrial fibrillation screening mode when the frequent occurrence condition is satisfied.

As is clear from the above, according to the electronic sphygmomanometer and the atrial fibrillation determination method in an electronic sphygmomanometer of the present disclosure, it is possible to accurately determine whether or not there is a possibility that atrial fibrillation occurred in a relatively short time per one measurement occasion.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. An electronic sphygmomanometer that measures blood pressure based on a pulse wave of an artery passing through a site to be measured, the electronic sphygmomanometer comprising:

a cuff configured to be worn on the site to be measured;

a pump and a valve each fluidly connected to the cuff;

a pressure sensor configured to detect a pressure of the cuff; and a processor, wherein, in a normal blood pressure measurement mode, the processor is configured to:

act as a cuff pressure control unit to perform control to pressurize the cuff by supplying fluid from the pump to the cuff or depressurize the cuff by discharging fluid from the cuff through the valve while acquiring, from the pressure sensor, a cuff pressure signal representing the pressure of the cuff;

act as a blood pressure measurement unit to extract a pulse wave signal representing a pulse wave superimposed on the cuff pressure signal and to measure blood pressure based on the pulse wave signal;

act as a pulse wave interval calculation unit to obtain, for each one measurement occasion of a subject, a data group representing pulse wave intervals based on the pulse wave signal obtained from only one blood pressure measurement performed in one pressurization process or one depressurization process;

wherein each one measurement occasion is an occasion for blood pressure measurement in which the subject wears the cuff once on the site to be measured, and is selected from one morning measurement occasion, one daytime measurement occasion belonging to a time period different from the morning measurement occasion, or one nighttime measurement occasion belonging to a time period different from the morning and daytime measurement occasions;

act as a first determination unit to aggregate data groups for three or more measurement occasions of the subject and to determine whether or not there is a possibility that atrial fibrillation has occurred based on whether or not irregular pulse wave data exceeding a predetermined allowable range with respect to an average value of the pulse wave intervals exists in the aggregated data groups;

wherein the three measurement occasions are selected from the morning measurement occasion, the daytime measurement occasion, and/or the nighttime measurement occasion, and every time interval between neighboring measurement occasions in date and time order among the three measurement occasions is within one day as a predetermined allowable period;

wherein the electronic sphygmomanometer has, under control of the processor, the normal blood pressure measurement mode in which blood pressure measurement is performed only once per one measurement occasion, and an atrial fibrillation screening mode in which blood pressure measurement is repeated three or more times per one measurement occasion; and wherein, in the normal blood pressure measurement mode, the processor is configured to:

act as a second determination unit to determine whether or not the irregular pulse wave data in the aggregated data groups satisfies a predetermined frequent occurrence condition based on presence or absence of occurrence of an irregular pulse wave for each one measurement occasion; and act as a notification unit to provide a notification prompting switching from the normal blood pressure measurement mode to the atrial fibrillation screening mode when the frequent occurrence condition is satisfied.

2. The electronic sphygmomanometer according to claim 1, wherein when acting as the first determination unit, the processor is configured to:

obtain, for each one measurement occasion, a respective average value of the pulse wave intervals for each data group corresponding to the one measurement occasion, determine whether or not irregular pulse wave data exists in the data group for the one measurement occasion, and obtain an individual determination result representing whether or not an irregular pulse wave has occurred for each one measurement occasion, and determine that there is a possibility that atrial fibrillation has occurred only when the individual determination results indicating occurrence of an irregular pulse wave are obtained for two or more measurement occasions out of the three measurement occasions.

3. The electronic sphygmomanometer according to claim 2, further comprising a memory configured to store the individual determination result for each one measurement occasion in association with a measurement date and time, wherein, when acting as the first determination unit, the processor is configured to:

search for the individual determination results stored in the memory backward from the latest one, and determine whether or not there is a possibility that atrial fibrillation has occurred only when the individual determination results for the three or more measurement occasions are available with satisfying a condition that every time interval between the neighboring measurement occasions is within the allowable period.

4. The electronic sphygmomanometer according to claim 3, wherein the frequent occurrence condition is selected from:

(i) a condition that irregular pulse wave data exists in each of the data groups representing pulse wave intervals for the latest two measurement occasions;

(ii) a condition that irregular pulse wave data exists in each of the data groups representing pulse wave intervals for a majority of the latest five measurement occasions;

(iii) a condition that irregular pulse wave data exists in each of the data groups representing pulse wave intervals for the latest two measurement occasions belonging to the same daily time period; or (iv) a condition that irregular pulse wave data exists in each of the data groups representing pulse wave intervals for a majority of the latest five measurement occasions belonging to the same daily time period.

5. An atrial fibrillation determination method in an electronic sphygmomanometer according to claim 1, the atrial fibrillation determination method comprising:

in the normal blood pressure measurement mode, performing control to pressurize or depressurize the cuff while acquiring a cuff pressure signal representing a pressure of the cuff;

extracting a pulse wave signal representing a pulse wave superimposed on the cuff pressure signal and measuring blood pressure based on the pulse wave signal;

obtaining, for each one measurement occasion of a subject, a data group representing pulse wave intervals based on the pulse wave signal obtained from only one blood pressure measurement performed in one pressurization process or one depressurization process;

aggregating data groups for three or more measurement occasions of the subject and determining whether or not there is a possibility that atrial fibrillation has occurred based on whether or not irregular pulse wave data exists in the aggregated data groups;

determining whether or not the irregular pulse wave data in the aggregated data groups satisfies the frequent occurrence condition; and providing a notification prompting switching from the normal blood pressure measurement mode to the atrial fibrillation screening mode when the frequent occurrence condition is satisfied.

6. An electronic sphygmomanometer that measures blood pressure based on a pulse wave of an artery passing through a site to be measured, the electronic sphygmomanometer comprising:

a cuff configured to be worn on the site to be measured;

a pump and a valve each fluidly connected to the cuff;

a pressure sensor configured to detect a pressure of the cuff; and a processor, wherein, in a normal blood pressure measurement mode, the processor is configured to:

act as a cuff pressure control unit to perform control to pressurize the cuff by supplying fluid from the pump to the cuff or depressurize the cuff by discharging fluid from the cuff through the valve while acquiring, from the pressure sensor, a cuff pressure signal representing the pressure of the cuff;

act as a blood pressure measurement unit to extract a pulse wave signal representing a pulse wave superimposed on the cuff pressure signal and to measure blood pressure based on the pulse wave signal;

act as a pulse wave interval calculation unit to obtain, for each one measurement occasion of a subject, a data group representing pulse wave intervals based on the pulse wave signal obtained from only one blood pressure measurement performed in one pressurization process or one depressurization process;

wherein each one measurement occasion is an occasion for blood pressure measurement in which the subject wears the cuff once on the site to be measured, and is selected from one morning measurement occasion, one daytime measurement occasion belonging to a time period different from the morning measurement occasion, or one nighttime measurement occasion belonging to a time period different from the morning and daytime measurement occasions;

act as a first determination unit to aggregate data groups for three or more measurement occasions of the subject and to determine whether or not there is a possibility that atrial fibrillation has occurred based on whether or not irregular pulse wave data exceeding a predetermined allowable range with respect to an average value of the pulse wave intervals exists in the aggregated data groups;

wherein the three measurement occasions are selected from the morning measurement occasion, the daytime measurement occasion, and/or the nighttime measurement occasion, and every time interval between neighboring measurement occasions in date and time order among the three measurement occasions is within one day as a predetermined allowable period;

wherein the electronic sphygmomanometer has, under control of the processor, the normal blood pressure measurement mode in which blood pressure measurement is performed only once per one measurement occasion, and an atrial fibrillation screening mode in which blood pressure measurement is repeated three or more times per one measurement occasion; and wherein, in the normal blood pressure measurement mode, the processor is configured to:

act as a second determination unit to determine whether or not the irregular pulse wave data in the aggregated data groups satisfies a predetermined frequent occurrence condition based on presence or absence of occurrence of an irregular pulse wave for each one measurement occasion; and act as a mode control unit to perform control to switch from the normal blood pressure measurement mode to the atrial fibrillation screening mode when the frequent occurrence condition is satisfied.

* * * * *